(12) United States Patent
Murphy et al.

(10) Patent No.: US 11,019,810 B2
(45) Date of Patent: *Jun. 1, 2021

(54) NON-HUMAN ANIMALS HAVING A HUMANIZED SIGNAL-REGULATORY PROTEIN GENE

(71) Applicant: Regeneron Pharmaceuticals, Inc., Tarrytown, NY (US)

(72) Inventors: Andrew J. Murphy, Croton-on-Hudson, NY (US); O. Gavin Thurston, Briarcliff Manor, NY (US); Bindu Varghese, Avondale, PA (US); Cagan Gurer, Chappaqua, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/541,334

(22) Filed: Aug. 15, 2019

(65) Prior Publication Data

US 2020/0187468 A1 Jun. 18, 2020

Related U.S. Application Data

(63) Continuation of application No. 16/238,589, filed on Jan. 3, 2019, now Pat. No. 10,426,146, which is a continuation of application No. 15/866,632, filed on Jan. 10, 2018, now Pat. No. 10,206,379, which is a continuation of application No. 15/615,298, filed on Jun. 6, 2017, now Pat. No. 9,901,083, which is a continuation of application No. 15/263,916, filed on Sep. 13, 2016, now Pat. No. 9,700,027, which is a continuation of application No. 14/882,531, filed on Oct. 14, 2015, now Pat. No. 9,462,794, which is a continuation of application No. 14/493,745, filed on Sep. 23, 2014, now Pat. No. 9,193,977.

(60) Provisional application No. 61/881,261, filed on Sep. 23, 2013.

(51) Int. Cl.

| A01K 67/027 | (2006.01) |
| C07K 14/705 | (2006.01) |
| C12N 15/90 | (2006.01) |
| A61K 49/00 | (2006.01) |
| C12N 15/85 | (2006.01) |
| C12N 15/89 | (2006.01) |
| G01N 33/50 | (2006.01) |
| C12N 9/16 | (2006.01) |
| C07K 16/28 | (2006.01) |

(52) U.S. Cl.
CPC ...... *A01K 67/0278* (2013.01); *A61K 49/0008* (2013.01); *C07K 14/70596* (2013.01); *C12N 15/8509* (2013.01); *C12N 15/89* (2013.01); *C12N 15/902* (2013.01); *C12N 15/907* (2013.01); *A01K 2207/12* (2013.01); *A01K 2207/15* (2013.01); *A01K 2217/05* (2013.01); *A01K 2217/052* (2013.01); *A01K 2217/054* (2013.01); *A01K 2217/072* (2013.01); *A01K 2227/10* (2013.01); *A01K 2227/105* (2013.01); *A01K 2267/01* (2013.01); *A01K 2267/0331* (2013.01); *A01K 2267/0381* (2013.01); *A01K 2267/0387* (2013.01); *C07K 14/70503* (2013.01); *C07K 16/2809* (2013.01); *C07K 16/2887* (2013.01); *C07K 2317/31* (2013.01); *C07K 2319/00* (2013.01); *C12N 9/16* (2013.01); *C12N 2015/8518* (2013.01); *C12N 2015/8527* (2013.01); *C12N 2015/8572* (2013.01); *C12N 2800/30* (2013.01); *C12Y 301/03048* (2013.01); *G01N 33/5011* (2013.01); *G01N 33/5088* (2013.01); *G01N 2500/04* (2013.01); *G01N 2500/10* (2013.01)

(58) Field of Classification Search
CPC ............ A01K 67/0278; A01K 2207/12; A01K 2227/10; A01K 2207/15; A01K 2217/072; A01K 2267/0331; A01K 2267/0387; A01K 2267/0381; A01K 49/0008; C07K 14/70596; C12N 15/907; C12N 15/8509; C12N 15/902; C12N 2015/852718
USPC .......... 800/13, 3, 10, 21, 25; 435/320.1, 353
See application file for complete search history.

(56) References Cited

U.S. PATENT DOCUMENTS

| 9,127,292 B2 | 9/2015 | Murphy et al. |
| 9,193,977 B2 | 11/2015 | Murphy et al. |
| 9,462,794 B2 * | 10/2016 | Murphy ........... C07K 14/70596 |

(Continued)

FOREIGN PATENT DOCUMENTS

| CN | 103492576 A | 1/2014 |
| RU | 2 425 880 C2 | 2/2011 |

(Continued)

OTHER PUBLICATIONS

Willinger et al. (2011) PNAS, vol. 108(6), 2390-2395.*

(Continued)

*Primary Examiner* — Anne Marie S Wehbe
(74) *Attorney, Agent, or Firm* — Scully, Scott, Murphy & Presser, P.C.; Elysa Goldberg

(57) ABSTRACT

Genetically modified non-human animals and methods and compositions for making and using the same are provided, wherein the genetic modification comprises a humanization of an endogenous signal-regulatory protein gene, in particular a humanization of a SIRPα gene. Genetically modified mice are described, including mice that express a human or humanized SIRPα protein from an endogenous SIRPα locus.

14 Claims, 8 Drawing Sheets

Specification includes a Sequence Listing.

(56) References Cited

U.S. PATENT DOCUMENTS

| | | | |
|---|---|---|---|
| 9,700,027 B2* | 7/2017 | Murphy | C12N 9/16 |
| 9,901,083 B2 | 2/2018 | Murphy et al. | |
| 10,206,379 B2 | 2/2019 | Murphy et al. | |
| 10,426,146 B2* | 10/2019 | Murphy | C07K 16/2887 |
| 2013/0111616 A1 | 5/2013 | MacDonald et al. | |
| 2013/0111617 A1 | 5/2013 | MacDonald et al. | |
| 2013/0117873 A1 | 5/2013 | Wang et al. | |
| 2013/0340105 A1* | 12/2013 | Flavell | C07K 14/70503 800/18 |
| 2014/0134662 A1 | 5/2014 | Flavell et al. | |
| 2014/0245466 A1 | 8/2014 | MacDonald et al. | |
| 2014/0245467 A1 | 8/2014 | MacDonald et al. | |
| 2015/0089678 A1 | 3/2015 | Murphy et al. | |
| 2016/0050896 A1 | 2/2016 | Murphy et al. | |
| 2016/0374321 A1 | 12/2016 | Murphy et al. | |
| 2017/0265442 A1 | 9/2017 | Murphy et al. | |
| 2018/0139941 A1 | 5/2018 | Murphy et al. | |
| 2019/0124895 A1 | 5/2019 | Murphy et al. | |

FOREIGN PATENT DOCUMENTS

| | | |
|---|---|---|
| WO | 2011/044050 A2 | 4/2011 |
| WO | 2012/040207 A2 | 3/2012 |
| WO | 2012/112544 A2 | 8/2012 |
| WO | 2013/063556 A1 | 5/2013 |
| WO | 2013/192030 A1 | 12/2013 |
| WO | 2014/039782 A2 | 3/2014 |

OTHER PUBLICATIONS

Navarro-Alvarez et al. (2011) Cellular and Molecular Immunology, vol. 8,285-288.*
Barclay et al. (2006) Nature Reviews, vol. 6, 457-464.*
Brooke et al. (2004) J. Immunol., vol. 173,2562-2570.*
Sano et al. (1999) Biochem. J., vol. 344, 667-675.*
Verneris et al. (2005) Clin. Canc. Res., vol. 11(12), 4561-4570.*
Kawamata M. et al., "Generation of Genetically Modified Rats from Embryonic Stem Cells", PNAS 107 (32):14223-14228 (Aug. 10, 2010).
European Examination Report dated Apr. 8, 2020 received in European Patent Application No. 18 192 264.2.
Anderson P., "Post-Transcriptional Control of Cytokine Production", Nature Immunology 9(4):353-359 (Apr. 2008).
Barclay, A.N. et al., "The SIRP Family of Receptors and Immune Regulation", Nature Reviews—Immunology 6:457-464 (Jun. 2006).
Brook G. et al., "Human Lymphocytes Interact Directly With CD47 Through a Novel Member of the Signal Regulatory Protein (SIRP) Family", The Journal of Immunology 173:2562-2570 (2004).
Harari D. et al., "Bridging the Species Divide: Transgenic Mice Humanized for Type-I Interferon Response", PLoS ONE 9(1):e84259, XP055553720, DOI:10.1371/journal.pone.0084259 (Jan. 9, 2014).
Inagaki, K. et al., "SHPS-1 Regulates Integrin-Mediated Cytoskeletal Reorganization and Cell Motility", The EMBO Journal 19(24):6721-6731 (2000).
Ishikawa-Sekigami, T. et al., "SHPS-1 Promotes the Survival of Circulating Erythrocytes Through Inhibition of Phagocytosis by Splenic Macrophages", Blood 107(1):341-348 (Jan. 1, 2006).
Jacob H.J. et al., "Gene Targeting in the Rat: Advances and Opportunities", Trends in Genetics 26(12):510-518 (Dec. 2010).
Legrand N. et al., "Functional CD47/Signal Regulatory Protein Alpha (SIRPα) Interaction is Required for Optimal Human T- and Natural Killer-(NK) Cell Homeostatis in Vivo", PNAS 108(32):13224-13229 (Aug. 9, 2011).
Navarro-Alvarez N. et al., "CD47: A New Player in Phagocytosis and Xenograft Rejection", Cellular & Molecular Immunology 8:285-288 (2011).
Oldenborg P-A et al., "Role of CD47 as a Marker of Self on Red Blood Cells", Science 288:2051-2054 (Jun. 16, 2000).
Rongvaux A. et al., "Human Thrombopoietin Knockin Mice Efficiently Support Human Hematopoiesis in Vivo", PNAS 108(6):2378-2383 (Feb. 8, 2011).
Sano S-I et al., "Gene Structure of Mouse BIT/SHPS-1", Biochem J. 344:667-675 (1999).
Shultz L.D. et al., "Multiple Defects in Innate and Adaptive Immunologic Function in NOD/LtSz-Scid Mice", The Journal of Immunology 154:180-191 (1995).
Strowig T. et al., "Transgenic Expression of Human Signal Regulatory Protein Alpha in Rag2-/-γc-/- Mice Improves Engraftment of Human Hematopoietic Cells in Humanized Mice", PNAS 108(32):13218-13223 (Aug. 9, 2011).
Strowig T. et al., "Transgenic Expression of Human Signal Regulatory Protein Alpha in Rag2-/-γc-/- Mice Improves Engraftment of Human Hematopoietic Cells in Humanized Mice", PNAS, Supporting Material, pp. 1-4 (Aug. 9, 2011).
Takenaka K. et al., "Polymorphism in Sirpa Modulates Engraftment of Human Hematopoietic Stem Cells", Nature Immunology 8(12):1313-1323 (Dec. 2007).
Takenaka K. et al., "Polymorphism in Sirpa Modulates Engraftment of Human Hematopoietic Stem Cells", Nature Immunology, Supplemental Material, pp. 1-5 (Dec. 2007).
Tomizawa T. et al., "Resistance to Experimental Autoimmune Encephalomyelitis and Impaired T Cell Priming by Dendritic Cells in Src Homology 2 Domain-Containing Protein Tyrosine Phosphatase Substrate-1 Mutant Mice", The Journal of Immunology 179(2):869-877 (Jul. 15, 2007).
Tong C. et al., "Production of p53 Gene Knockout Rats by Homologous Recombination in Embryonic Stem Cells", Nature 467:211-215 (Sep. 9, 2010).
Valenzuela D.M. et al., "High-Throughput Engineering of the Mouse Genome Coupled with High-Resolution Expression Analysis", Nature Biotechnology 21(6):652-659 (Jun. 2003).
Verneris M.R. et al., "Low Levels of Her2/Neu Expressed by Ewing's Family Tumor Cell Lines Can Redirect Cytokine-Induced Killer Cells", Clinical Cancer Research 11(12):4561-4570 (Jun. 15, 2005).
Willinger T. et al., "Human IL-3/GM-CSF Knock-in Mice Support Human Alveolar Macrophage Development and Human Immune Responses in the Lung", PNAS 108(6):2390-2395 (Feb. 8, 2011), including Willinger supporting information pp. 1-6.
Willinger T. et al., "Improving Human Hemato-Lymphoid-System Mice by Cytokine Knock-In Gene Replacement", Trends in Immunology 32(7):321-327 (Jul. 2011).
Yamao T. et al., "Negative Regulation of Platelet Clearance and of the Macrophage Phagocytic Response by the Transmembrane Glycoprotein SHPS-1", The Journal of Biological Chemistry 277(42):39833-39839 (Oct. 18, 2002).
International Search Report and Written Opinion dated Mar. 9, 2015 received from Application No. PCT/US2014/056910.
Russian Office Action and Search Report dated Mar. 29, 2018 received in Russian Patent Application No. 2016110462, together with an English-language translation.
Chinese Office Action dated Mar. 2, 2021 received in Chinese Application No. 201810267662.3, together with an English-language translation.

* cited by examiner

NON-HUMAN ANIMALS HAVING A HUMANIZED SIGNAL-REGULATORY PROTEIN GENE

CROSS REFERENCE TO RELATED APPLICATION

This is a continuation of U.S. patent application Ser. No. 16/238,589, filed Jan. 3, 2019, which is a continuation of U.S. patent application Ser. No. 15/866,632, filed Jan. 10, 2018, now U.S. Pat. No. 10,206,379, which is a continuation of U.S. patent application Ser. No. 15/615,298, filed Jun. 6, 2017, now U.S. Pat. No. 9,901,083, which is a continuation of U.S. patent application Ser. No. 15/263,916, filed Sep. 13, 2016, now U.S. Pat. No. 9,700,027, which is a continuation of U.S. patent application Ser. No. 14/882,531, filed Oct. 14, 2015, now U.S. Pat. No. 9,462,794, which is a continuation of U.S. patent application Ser. No. 14/493,745, filed Sep. 23, 2014, now U.S. Pat. No. 9,193,977, which claims the benefit of priority of U.S. Provisional Application No. 61/881,261, filed Sep. 23, 2013, the entire contents of which are incorporated herein by reference.

BACKGROUND

The immune system is composed of several different cell types that are involved in multiple highly regulated processes and together generate immune responses that are effective in eliminating foreign proteins. Further, these same immune cells have been found to possess a self-awareness property by virtue of, inter alia, regulatory membrane proteins that regulate cell-to-cell interactions. Such communication is critical for the survival of such organisms, as these same proteins are suggested to be an important determinant of transplant engraftment. However, no in vivo system exists to determine the molecular aspects of human immune cell-to-cell interactions and its regulation. Such a system provides a source for assays in human hematopoietic and immune system related functions in vivo, identification of novel therapies and vaccines.

SUMMARY OF INVENTION

The present invention encompasses the recognition that it is desirable to engineer non-human animals to permit improved engraftment of human hematopoietic stem cells. The present invention also encompasses the recognition that non-human animals having a humanized SIRPα gene and/or otherwise expressing, containing, or producing a human or humanized SIRPα protein are desirable, for example for use in engraftment of human hematopoietic stem cells.

In some embodiments, a non-human animal of the present invention expresses a SIRPα polypeptide comprising an extracellular portion of a human SIRPα protein and intracellular portion of a mouse SIRPα protein.

In some embodiments, an extracellular portion of a human SIRPα protein comprises amino acids corresponding to residues 28-362 of a human SIRPα protein that appears in SEQ ID NO: 4.

In some embodiments, an extracellular portion of a human SIRPα protein shares a percent identity of at least 50%, at least 55%, at least 60%, at least 65%, at least 70%, at least 75%, at least 80%, at least 85%, at least 90%, at least 95%, or at least 98% with a corresponding extracellular portion of a human SIRPα protein that appears in Table 3. In some embodiments, an extracellular portion of a human SIRPα protein shares 100% identity (or identical) with a corresponding extracellular portion of a human SIRPα protein that appears in Table 3.

In some embodiments, a non-human animal of the present invention does not also express an endogenous non-human SIRPα protein. In some embodiments, the non-human animal is a rodent and does not also express an endogenous rodent SIRPα protein. In some embodiments, the non-human animal is a mouse and does not also express an endogenous mouse SIRPα protein having a sequence that appears in Table 3.

In some embodiments, the present invention provides a non-human animal comprising a SIRPα gene that comprises exons 2, 3 and 4 of a human SIRPα gene operably linked to a non-human SIRPα promoter.

In some embodiments, a SIRPα gene of a non-human animal of the present invention comprises exons 1, 5, 6, 7 and 8 of an endogenous non-human SIRPα gene.

In various embodiments, a non-human animal of the present invention is a rodent. In some certain embodiments, a rodent of the present invention is selected from a mouse or a rat.

In some embodiments, the present invention provides a SIRPα polypeptide encoded by the gene of a non-human animal as described herein.

In some embodiments, the present invention provides a cell or tissue isolated from a non-human animal as described herein. In some embodiments, a cell is selected from a lymphocyte (e.g., a B or T cell), a myeloid cell (e.g., a macrophage, a neutrophil, a granulocyte, a myeloid dendritic cell, and a mast cell), and a neuron. In some embodiments, a tissue is selected from adipose, bladder, brain, breast, bone marrow, eye, heart, intestine, kidney, liver, lung, lymph node, muscle, pancreas, plasma, serum, skin, spleen, stomach, thymus, testis, ovum, and/or a combination thereof.

In some embodiments, the present invention provides an isolated mouse cell or tissue whose genome includes a SIRPα gene that encodes the extracellular portion of a human SIRPα protein linked to the intracellular portion of a mouse SIRPα protein. In some embodiments, a SIRPα gene of the present invention is operably linked to a mouse SIRPα promoter. In some embodiments, a SIRPα gene of the present invention comprises exons 2, 3, and 4 of a human SIRPα gene.

In some embodiments, the present invention provides a non-human embryonic stem (ES) cell whose genome comprises a SIRPα gene as described herein. In some embodiments, the ES cell comprises exons 2, 3 and 4 of a human SIRPα gene operably linked to a non-human SIRPα promoter. In some certain embodiments, the ES cell is a rodent ES cell. In some embodiments, a non-human embryonic stem cell of the present invention is a mouse or rat embryonic stem cell.

In some embodiments, the present invention provides a non-human embryo comprising, made from, obtained from, or generated from a non-human embryonic stem cell comprising a SIRPα gene as described herein. In some embodiments, a non-human embryo of the present invention is a rodent embryo. In some embodiments, a rodent embryo as described herein is a mouse or rat embryo.

In some embodiments, the present invention provides a method of making a non-human animal that expresses a SIRPα protein from an endogenous SIRPα locus, wherein the SIRPα protein comprises a human sequence, the method comprising targeting an endogenous SIRPα locus in a non-human ES cell with a genomic fragment comprising a nucleotide sequence that encodes a human SIRPα protein in whole or in part; obtaining a modified non-human ES cell comprising an endogenous SIRPα locus that comprises said human sequence, and, creating a non-human animal using said modified ES cell.

In some embodiments, said nucleotide sequence comprises exons 2, 3 and 4 of a human SIRPα gene. In some embodiments, said nucleotide sequence comprises exons 2, 3 and 4 of a human SIRPα gene having a sequence at least 50%, at least 55%, at least 60%, at least 65%, at least 70%, at least 75%, at least 80% N, at least 85%, at least 90%, at least 95%, or at least 98% identical to a human SIRPα gene that appears in Table 3.

In some embodiments, said nucleotide sequence encodes amino acid residues 28-362 of a human SIRPα protein. In some embodiments, said nucleotide sequence encodes amino acid residues 28-362 of a human SIRPα protein having a sequence at least 50%, at least 55%, at least 60%, at least 65%, at least 70% N, at least 75%, at least 80%, at least 85%, at least 90%, at least 95%, or at least 98% identical to a human SIRPα protein that appears in Table 3.

In some embodiments, the present invention provides a method of providing a mouse whose genome includes a SIRPα gene that encodes the extracellular portion of a human SIRPα protein linked to the intracellular portion of a mouse SIRPα protein, the method comprising modifying the genome of a mouse so that it comprises a SIRPα gene that encodes the extracellular portion of a human SIRPα protein linked to the intracellular portion of a mouse SIRPα protein thereby providing said mouse. In some embodiments, the SIRPα gene is a SIRPα gene as described herein. In some embodiments, the SIRPα gene comprises exons 2, 3, and 4 of a human SIRPα gene.

In some embodiments, the present invention provides a method of engrafting human cells into a mouse, the method comprising steps of providing a mouse whose genome comprises a SIRPα gene that encodes the extracellular portion of a human SIRPα protein linked to the intracellular portion of a mouse SIRPα protein, and transplanting one or more human cells into the mouse. In some certain embodiments, the method further comprises as step assaying engraftment of the one or more human cells in the mouse. In some certain embodiments, the step of assaying comprises comparing the engraftment of the one or more human cells to the engraftment in one or more wild-type mice. In some certain embodiments, the step of assaying comprises comparing the engraftment of the one or more human cells to the engraftment in one or more mice whose genome does not comprise a SIRPα gene that encodes the extracellular portion of a human SIRPα protein linked to the intracellular portion of a mouse SIRPα protein.

In some embodiments, the human cells are hematopoietic stem cells. In some embodiments, the human cells are transplanted intravenously. In some embodiments, the human cells are transplanted intraperitoneally. In some embodiments, the human cells are transplanted subcutaneously.

In some embodiments, the present invention provides a method comprising the steps of providing one or more cells whose genome includes a SIRPα gene that encodes the extracellular portion of a human SIRPα protein linked to the intracellular portion of a mouse SIRPα protein, incubating the one or more cells with a labeled substrate, and measuring phagocytosis of the labeled substrate by the one or more cells. In some embodiments, the cells are mouse cells.

In some embodiments, the substrate is fluorescently labeled. In some embodiments, the substrate is labeled with an antibody. In some embodiments, the substrate is one or more red blood cells. In some embodiments, the substrate is one or more bacterial cells.

In some embodiments, the present invention provides a method comprising the steps of providing a mouse whose genome includes a SIRPα gene that encodes the extracellular portion of a human SIRPα protein linked to the intracellular portion of a mouse SIRPα protein, exposing the mouse to an antigen, and measuring phagocytosis of the antigen by one or more cells of the mouse. In some embodiments, the step of exposing comprises exposing the mouse to an antigen that is fluorescently labeled. In some embodiments, the step of exposing comprises exposing the mouse to one or more cells that comprise the antigen. In some embodiments, the step of exposing comprises exposing the mouse to one or more human cells comprising the antigen. In some embodiments, the step of exposing comprises exposing the mouse to one or more bacterial cells comprising the antigen.

In various embodiments, a SIRPα gene of the present invention comprises exons 2, 3, and 4 of a human SIRPα gene. In various embodiments, an extracellular portion of a human SIRPα protein of the present invention comprises amino acids corresponding to residues 28-362 of a human SIRPα protein that appears in Table 3. In various embodiments, a SIRPα gene of the present invention is operably linked to a mouse SIRPα promoter.

In some embodiments, the present invention provides a non-human animal obtainable by methods as described herein. In some certain embodiments, non-human animals of the present invention do not detectably express an extracellular portion of an endogenous SIRPα protein.

In some embodiments, the present invention provides methods for identification or validation of a drug or vaccine, the method comprising the steps of delivering a drug or vaccine to a non-human animal as described herein, and monitoring one or more of the immune response to the drug or vaccine, the safety profile of the drug or vaccine, or the effect on a disease or condition. In some embodiments, monitoring the safety profile includes determining if the non-human animal exhibits a side effect or adverse reaction as a result of delivering the drug or vaccine. In some embodiments, a side effect or adverse reaction is selected from morbidity, mortality, alteration in body weight, alteration of the level of one or more enzymes (e.g., liver), alteration in the weight of one or more organs, loss of function (e.g., sensory, motor, organ, etc.), increased susceptibility to one or more diseases, alterations to the genome of the non-human animal, increase or decrease in food consumption and complications of one or more diseases.

In some embodiments, the present invention provides use of a non-human animal of the present invention in the development of a drug or vaccine for use in medicine, such as use as a medicament.

In some embodiments, the present invention provides use of a non-human animal described herein to assess the efficacy of a therapeutic drug targeting human cells. In various embodiments, a non-human animal of the present invention is transplanted with human cells, and a drug candidate targeting such human cells is administered to the animal. The efficacy of the drug is determined by monitoring the human cells in the non-human animal after the administration of the drug.

In various embodiments, non-human animals of the present invention are rodents, preferably a mouse or a rat.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWING

The drawing included herein is for illustration purposes only not for limitation.

DEFINITIONS

Figure 1:
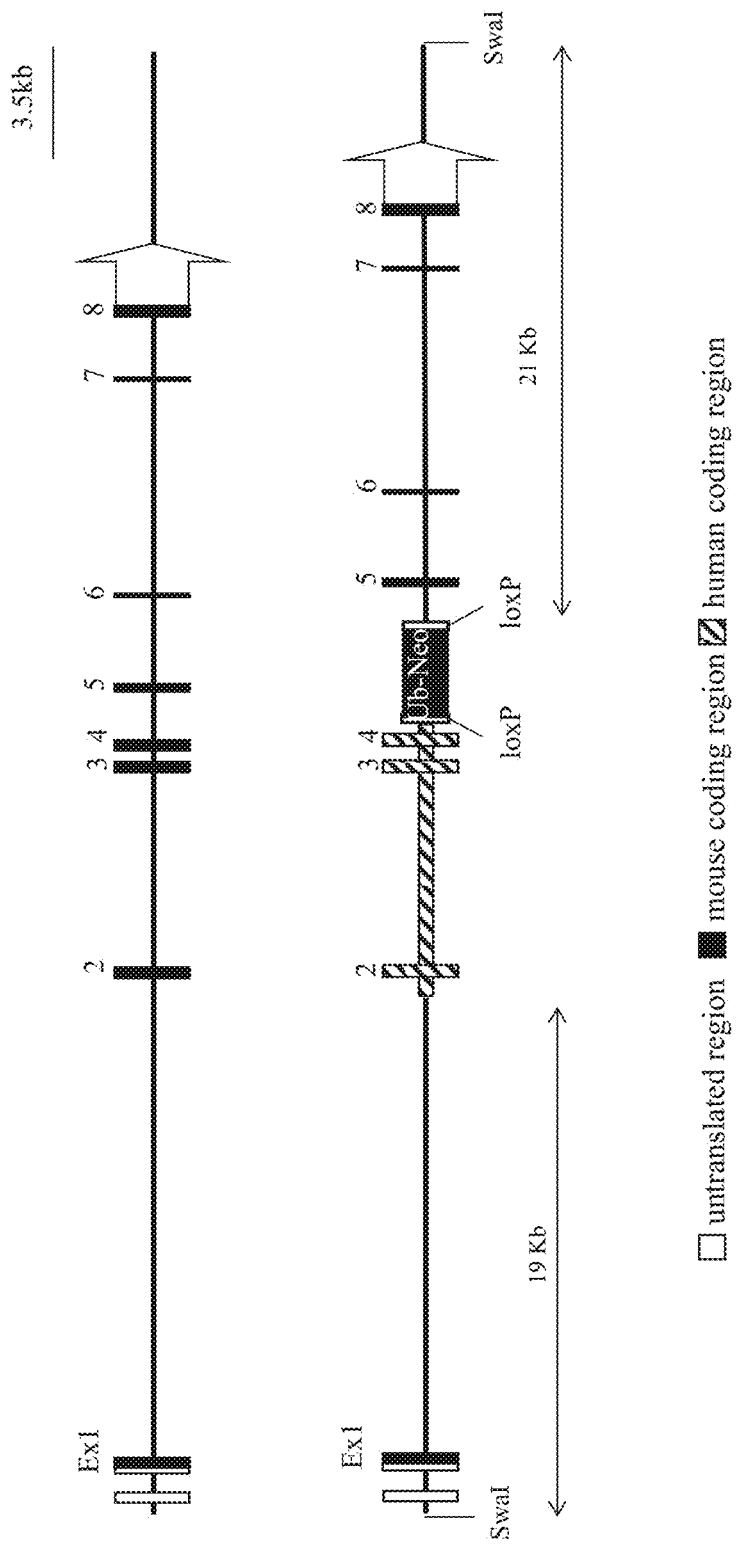
FIG. 1 shows a diagram, not to scale, of an endogenous murine SIRPα gene (top) with each exon numbered. A humanized endogenous SIRPα gene (bottom) is shown containing exons 2-4 of a human SIRPα gene and a neomycin selection cassette (Ub-Neo) flanked by site-specific recombinase recognition sites (e.g., loxP). The targeted insertion of exons 2-4 of a human SIRPα gene results in an endogenous gene that expresses a humanized SIRPα gene having an extracellular region corresponding to a human SIRPα protein.

This invention is not limited to particular methods, and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. All publications mentioned are hereby incorporated by reference.

The term "approximately" as applied herein to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The term "biologically active" as used herein refers to a characteristic of any agent that has activity in a biological system, in vitro or in vivo (e.g., in an organism). For instance, an agent that, when present in an organism, has a biological effect within that organism, is considered to be biologically active. In particular embodiments, where a protein or polypeptide is biologically active, a portion of that protein or polypeptide that shares at least one biological activity of the protein or polypeptide is typically referred to as a "biologically active" portion.

The term "comparable", as used herein, refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

The term "conservative" as used herein to describe a conservative amino acid substitution refers to substitution of an amino acid residue by another amino acid residue having a side chain R group with similar chemical properties (e.g., charge or hydrophobicity). In general, a conservative amino acid substitution will not substantially change the functional properties of interest of a protein, for example, the ability of a receptor to bind to a ligand. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. In some embodiments, a conservative amino acid substitution can be substitution of any native residue in a protein with alanine, as used in, for example, alanine scanning mutagenesis. In some embodiments, a conservative substitution is made that has a positive value in the PAM250 log-likelihood matrix disclosed in Gonnet et al. (1992) Exhaustive Matching of the Entire Protein Sequence Database, Science 256:1443-45, hereby incorporated by reference. In some embodiments, the substitution is a moderately conservative substitution wherein the substitution has a nonnegative value in the PAM250 log-likelihood matrix.

The term "disruption" as used herein refers to the result of a homologous recombination event with a DNA molecule (e.g., with an endogenous homologous sequence such as a gene or gene locus. In some embodiments, a disruption may achieve or represent an insertion, deletion, substitution, replacement, missense mutation, or a frame-shift of a DNA sequence(s), or any combination thereof. Insertions may include the insertion of entire genes or fragments of genes, e.g. exons, which may be of an origin other than the endogenous sequence. In some embodiments, a disruption may increase expression and/or activity of a gene or gene product (e.g., of a protein encoded by a gene). In some embodiments, a disruption may decrease expression and/or activity of a gene or gene product. In some embodiments, a disruption may alter sequence of a gene or an encoded gene product (e.g., an encoded protein). In some embodiments, a disruption may truncate or fragment a gene or an encoded gene product (e.g., an encoded protein). In some embodiments, a disruption may extend a gene or an encoded gene product; in some such embodiments, a disruption may achieve assembly of a fusion protein. In some embodiments, a disruption may affect level but not activity of a gene or gene product. In some embodiments, a disruption may affect activity but not level of a gene or gene product. In some embodiments, a disruption may have no significant effect on level of a gene or gene product. In some embodiments, a disruption may have no significant effect on activity of a gene or gene product. In some embodiments, a disruption may have no significant effect on either level or activity of a gene or gene product.

The phrase "endogenous locus" or "endogenous gene" as used herein refers to a genetic locus found in a parent or reference organism prior to introduction of a disruption, deletion, replacement, alteration, or modification as described herein. In some embodiments, the endogenous locus has a sequence found in nature. In some embodiments, the endogenous locus is wild type. In some embodiments, the reference organism is a wild-type organism. In some embodiments, the reference organism is an engineered organism. In some embodiments, the reference organism is a laboratory-bred organism (whether wild-type or engineered).

The phrase "endogenous promoter" refers to a promoter that is naturally associated, e.g., in a wild-type organism, with an endogenous gene.

The term "heterologous" as used herein refers to an agent or entity from a different source. For example, when used in reference to a polypeptide, gene, or gene product or present in a particular cell or organism, the term clarifies that the relevant polypeptide, gene, or gene product 1) was engineered by the hand of man; 2) was introduced into the cell or organism (or a precursor thereof) through the hand of man (e.g., via genetic engineering); and/or 3) is not naturally produced by or present in the relevant cell or organism (e.g., the relevant cell type or organism type).

The term "host cell", as used herein, refers to a cell into which a heterologous (e.g., exogenous) nucleic acid or protein has been introduced. Persons of skill upon reading this disclosure will understand that such terms refer not only to the particular subject cell, but also is used to refer to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, a host cell is or comprises a prokaryotic or eukaryotic cell. In general, a host cell is any cell that is suitable for receiving and/or producing a heterologous nucleic acid or protein, regardless of the Kingdom of life to which the cell is designated. Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, W138, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell). In some embodiments, a host cell is or comprises an isolated cell. In some embodiments, a host cell is part of a tissue. In some embodiments, a host cell is part of an organism.

The term "humanized", is used herein in accordance with its art-understood meaning to refer to nucleic acids or proteins whose structures (i.e., nucleotide or amino acid sequences) include portions that correspond substantially or identically with structures of a particular gene or protein found in nature in a non-human animal, and also include portions that differ from that found in the relevant particular non-human gene or protein and instead correspond more closely with comparable structures found in a corresponding human gene or protein. In some embodiments, a "humanized" gene is one that encodes a polypeptide having substantially the amino acid sequence as that of a human polypeptide (e.g., a human protein or portion thereof—e.g., characteristic portion thereof). To give but one example, in the case of a membrane receptor, a "humanized" gene may encode a polypeptide having an extracellular portion having an amino acid sequence as that of a human extracellular portion and the remaining sequence as that of a non-human (e.g., mouse) polypeptide. In some embodiments, a humanized gene comprises at least a portion of an DNA sequence of a human gene. In some embodiment, a humanized gene comprises an entire DNA sequence of a human gene. In some embodiments, a humanized protein comprises a sequence having a portion that appears in a human protein.

In some embodiments, a humanized protein comprises an entire sequence of a human protein and is expressed from an endogenous locus of a non-human animal that corresponds to the homolog or ortholog of the human gene.

The term "identity" as used herein in connection with a comparison of sequences, refers to identity as determined by a number of different algorithms known in the art that can be used to measure nucleotide and/or amino acid sequence identity. In some embodiments, identities as described herein are determined using a ClustalW v. 1.83 (slow) alignment employing an open gap penalty of 10.0, an extend gap penalty of 0.1, and using a Gonnet similarity matrix (MACVECTOR™ 10.0.2, MacVector Inc., 2008).

The term "isolated", as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%0, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

The phrase "non-human animal" as used herein refers to any vertebrate organism that is not a human. In some embodiments, a non-human animal is acyclostome, a bony fish, a cartilaginous fish (e.g., a shark or a ray), an amphibian, a reptile, a mammal, and a bird. In some embodiments, a non-human mammal is a primate, a goat, a sheep, a pig, a dog, a cow, or a rodent. In some embodiments, a non-human animal is a rodent such as a rat or a mouse.

The phrase "nucleic acid", as used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

The phrase "operably linked", as used herein, refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism. For example, in prokaryotes, such control sequences generally include promoter, ribosomal binding site, and transcription termination sequence, while in eukaryotes, typically, such control sequences include promoters and transcription termination sequence. The term "control sequences" is intended to include components whose presence is essential for expression and processing, and can also include additional components whose presence is advantageous, for example, leader sequences and fusion partner sequences.

The term "polypeptide", as used herein, refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man.

The term "recombinant", as used herein, is intended to refer to polypeptides (e.g., signal-regulatory proteins as described herein) that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29:128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) Current Opinion in Biotechnology 13:593-597, Little M. et al (2000) Immunology Today 21:364-370) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source. For example, in some embodiments, a recombinant polypeptide is comprised of sequences found in the genome of a source organism of interest (e.g., human, mouse, etc.). In some embodiments, a recombinant polypeptide has an amino acid sequence that resulted from mutagenesis (e.g., in vitro or in vivo, for example in a non-human animal), so that the amino acid sequences of the recombinant polypeptides are sequences that, while originating from and related to polypeptides sequences, may not naturally exist within the genome of a non-human animal in vivo.

The term "replacement" is used herein to refer to a process through which a "replaced" nucleic acid sequence (e.g., a gene) found in a host locus (e.g., in a genome) is removed from that locus and a different, "replacement" nucleic acid is located in its place. In some embodiments, the replaced nucleic acid sequence and the replacement nucleic acid sequences are comparable to one another in that, for example, they are homologous to one another and/or contain corresponding elements (e.g., protein-coding elements, regulatory elements, etc.). In some embodiments, a replaced nucleic acid sequence includes one or more of a promoter, an enhancer, a splice donor site, a splice receiver site, an intron, an exon, an untranslated region (UTR); in some embodiments, a replacement nucleic acid sequence includes one or more coding sequences. In some embodiments, a replacement nucleic acid sequence is a homolog of the replaced nucleic acid sequence. In some embodiments, a replacement nucleic acid sequence is an ortholog of the replaced sequence. In some embodiments, a replacement nucleic acid sequence is or comprises a human nucleic acid sequence. In some embodiments, including where the replacement nucleic acid sequence is or comprises a human nucleic acid sequence, the replaced nucleic acid sequence is or comprises a rodent sequence (e.g., a mouse sequence). The nucleic acid sequence so placed may include one or more regulatory sequences that are part of source nucleic acid sequence used to obtain the sequence so placed (e.g., promoters, enhancers, 5'- or 3'-untranslated regions, etc.). For example, in various embodiments, the replacement is a substitution of an endogenous sequence with a heterologous sequence that results in the production of a gene product from the nucleic acid sequence so placed (comprising the heterologous sequence), but not expression of the endogenous sequence; the replacement is of an endogenous genomic sequence with a nucleic acid sequence that encodes a protein that has a similar function as a protein encoded by the endogenous sequence (e.g., the endogenous genomic sequence encodes a SIRPα protein, and the DNA fragment encodes one or more human SIRPα proteins). In various embodiments, an endogenous gene or fragment thereof is replaced with a corresponding human gene or fragment thereof. A corresponding human gene or fragment thereof is a human gene or fragment that is an ortholog of, or is substantially similar or the same in structure and/or function, as the endogenous gene or fragment thereof that is replaced.

The phrase "signal-regulatory protein" or "SIRP" as used herein refers to a signal-regulatory protein receptor, e.g., a SIRPα receptor. SIRP genes include a plasma membrane receptor that is expressed on the surface of a cell and serves as a regulatory protein involved in interactions between membrane surface proteins on leukocytes. Within the SIRP genes, polymorphic variants have been described in human subjects. By way of illustration, nucleotide and amino acid sequences of a human and mouse SIRP genes are provided in Table 1. Persons of skill upon reading this disclosure will recognize that one or more endogenous SIRP receptor genes in a genome (or all) can be replaced by one or more heterologous SIRP genes (e.g., polymorphic variants, subtypes or mutants, genes from another species, humanized forms, etc.).

A "SIRP-expressing cell" as used herein refers to a cell that expresses a signal-regulatory protein receptor. In some embodiments, a SIRP-expressing cell expresses a signal-regulatory protein receptor on its surface. In some embodiments, a SIRP protein expressed on the surface of the cell in an amount sufficient to mediate cell-to-cell interactions via the SIRP protein expressed on the surface of the cell. Exemplary SIRP-expressing cells include neurons, lymphocytes, myeloid cells, macrophages, neutrophils, and natural killer (NK) cells. SIRP-expressing cells regulate the interaction of immune cells to regulate the immune response to various foreign antigens or pathogens. In some embodiments, non-human animals of the present invention demonstrate immune cell regulation via humanized SIRP receptors expressed on the surface of one more cells of the non-human animal.

The term "substantially" as used herein refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The phrase "substantial homology" as used herein refers to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized in Table 1 and 2.

TABLE 1

| Alanine | Ala | A | nonpolar | neutral | 1.8 |
|---|---|---|---|---|---|
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

TABLE 2

| Ambiguous Amino Acids | 3 Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul, et al., "Gapped BLAST and PSI-BLAST: a new generation of protein database search programs", *Nucleic Acids Res.* 25:3389-3402, 1997; Baxevanis, et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying homologous sequences, the programs mentioned above typically provide an indication of the degree of homology. In some embodiments, two sequences are considered to be substantially homologous if at least 50%, 55%, 60%, 65%, 70%, 75%, 80%, 85%, 90%, 91%, 92%, 93%, 94%, 95%, 96%, 97%, 98%, 99% or more of their corresponding residues are homologous over a relevant stretch of residues. In some embodiments, the relevant stretch is a complete sequence. In some embodiments, the relevant stretch is at least 9, 10, 11, 12, 13, 14, 15, 16, 17 or more residues. In some embodiments, the relevant stretch includes contiguous residues along a complete sequence. In some embodiments, the relevant stretch includes discontinuous residues along a complete sequence. In some embodiments, the relevant stretch is at least 10, 15, 20, 25, 30, 35, 40, 45, 50, or more residues.

The phrase "substantial identity" as used herein refers to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul, et al., Basic local alignment search tool, *J. Mol. Biol.*, 215(3): 403-410, 1990; Altschul, et al., *Methods in Enzymology*; Altschul et al., *Nucleic Acids Res.* 25:3389-3402, 1997; Baxevanis et al., *Bioinformatics: A Practical Guide to the Analysis of Genes and Proteins*, Wiley, 1998; and Misener, et al., (eds.), *Bioinformatics Methods and Protocols* (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, or more residues.

The phrase "targeting vector" or "targeting construct" as used herein refers to a polynucleotide molecule that comprises a targeting region. A targeting region comprises a sequence that is identical or substantially identical to a sequence in a target cell, tissue or animal and provides for integration of the targeting construct into a position within the genome of the cell, tissue or animal via homologous recombination. Targeting regions that target using site-specific recombinase recognition sites (e.g., loxP or Frt sites) are also included. In some embodiments, a targeting construct of the present invention further comprises a nucleic acid sequence or gene of particular interest, a selectable marker, control and or regulatory sequences, and other nucleic acid sequences that allow for recombination mediated through exogenous addition of proteins that aid in or facilitate recombination involving such sequences. In some embodiments, a targeting construct of the present invention further comprises a gene of interest in whole or in part, wherein the gene of interest is a heterologous gene that encodes a protein in whole or in part that has a similar function as a protein encoded by an endogenous sequence.

The term "variant", as used herein, refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity. As will be appreciated by those skilled in the art, any biological or chemical reference entity has certain characteristic structural elements. A variant, by definition, is a distinct chemical entity that shares one or more such characteristic structural elements. To give but a few examples, a small molecule may have a characteristic core structural element (e.g., a macrocycle core) and/or one or more characteristic pendent moieties so that a variant of the small molecule is one that shares the core structural element and the characteristic pendent moieties but differs in other pendent moieties and/or in types of bonds present (single vs. double, E vs. Z, etc) within the core, a polypeptide may have a characteristic sequence element comprised of a plurality of amino acids having designated positions relative to one another in linear or three-dimensional space and/or contributing to a particular biological function, a nucleic acid may have a characteristic sequence element comprised of a plurality of nucleotide residues having designated positions relative to on another in linear or three-dimensional space. For example, a variant polypeptide may differ from a reference polypeptide as a result of one or more differences in amino acid sequence and/or one or more differences in chemical moieties (e.g., carbohydrates, lipids, etc) covalently attached to the polypeptide backbone. In some embodiments, a variant polypeptide shows an overall sequence identity with a reference polypeptide that is at least 85%, 86%, 87%, 88%, 89%, 90%, 91%, 92%, 93%, 94%, 95%, 96%, 97%, or 99%. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide. In many embodiments, a polypeptide of interest is considered to be a "variant" of a parent or reference polypeptide if the polypeptide of interest has an amino acid sequence that is identical to that of the parent but for a small number of sequence alterations at particular positions. Typically, fewer than 20%, 15%, 10%, 9%, 8%, 7%, 6%, 5%, 4%, 3%, 2% of the residues in the variant are substituted as compared with the parent. In some embodiments, a variant has 10, 9, 8, 7, 6, 5, 4, 3, 2, or 1 substituted residue as compared with a parent. Often, a variant has a very small number (e.g., fewer than 5, 4, 3, 2, or 1) number of substituted functional residues (i.e., residues that participate in a particular biological activity). Furthermore, a variant typically has not more than 5, 4, 3, 2, or 1 additions or deletions, and often has no additions or deletions, as compared with the parent. Moreover, any additions or deletions are typically fewer than about 25, about 20, about 19, about 18, about 17, about 16, about 15, about 14, about 13, about 10, about 9, about 8, about 7, about 6, and commonly are fewer than about 5, about 4, about 3, or about 2 residues. In some embodiments, the parent or reference polypeptide is one found in nature. As will be understood by those of ordinary skill in the art, a plurality of variants of a particular polypeptide of interest may commonly be found in nature, particularly when the polypeptide of interest is an infectious agent polypeptide.

The term "vector", as used herein, refers to a nucleic acid molecule capable of transporting another nucleic acid to which it is associated. In some embodiment, vectors are capable of extra-chromosomal replication and/or expression of nucleic acids to which they are linked in a host cell such as a eukaryotic and/or prokaryotic cell. Vectors capable of directing the expression of operatively linked genes are referred to herein as "expression vectors."

The term "wild-type", as used herein, has its art-understood meaning that refers to an entity having a structure and/or activity as found in nature in a "normal" (as contrasted with mutant, diseased, altered, etc) state or context. Those of ordinary skill in the art will appreciate that wild type genes and polypeptides often exist in multiple different forms (e.g., alleles).

DETAILED DESCRIPTION

The present invention provides, among other things, improved and/or engineered non-human animals having humanized genetic material encoding a signal-regulatory protein (e.g., SIRPs) for assays in transplant engraftment, activation of phagocytosis and signal transduction. It is contemplated that such non-human animals provides an improvement in transplant engraftment of human cells. Therefore, the present invention is particularly useful for maintaining human hematopoietic cells in non-human animals. In particular, the present invention encompasses the humanization of a rodent SIRPα gene resulting in expression of a humanized protein on the plasma membrane surface of cells of the non-human animal. Such humanized proteins have the capacity to recognize engrafted human cells via engagement of humanized SIRPα proteins and ligands present on the surface of the engrafted human cells. In some embodiments, non-human animals of the present invention are capable of receiving transplanted human hematopoietic cells; in some embodiments, such non-human mammals develop and/or have an immune system comprising human cells. In some embodiments, humanized SIRPα proteins have sequence corresponding to amino acid residues 28-362 of a human SIRPα protein. In some embodiments, non-human animals of the present invention comprise an endogenous SIRPα gene that contains genetic material from the non-human animal and a heterologous species (e.g., a human). In some embodiments, non-human animals of the present invention comprise a humanized SIRPα gene, wherein the humanized SIRPα gene comprises exons 2, 3, and 4 of a human SIRPα gene.

Various aspects of the invention are described in detail in the following sections. The use of sections is not meant to limit the invention. Each section can apply to any aspect of the invention. In this application, the use of "or" means "and/or" unless stated otherwise.

Signal-Regulatory Protein (SIRP) Gene Family

Signal regulatory proteins (SIRPs) constitute a family of cell surface glycoproteins which are expressed on lymphocytes, myeloid cells (including macrophages, neutrophils, granulocytes, myeloid dendritic cells, and mast cells) and neurons (e.g., see Barclay and Brown, 2006, Nat Rev Immunol 6, 457-464). There are several reported SIRP genes and they can be categorized by their respective ligands and types of signaling in which they are involved. SIRPα (also referred to as CD172A, SHPS1, P84, MYD-1, BIT and PTPNS1) is expressed on immune cells of the myeloid lineage and functions as an inhibitory receptor via an immunoreceptor tyrosine-based inhibitory motif (ITIM). SIRPα expression has also been observed on neurons. Reported ligands for SIRPα include, most notably, CD47, but also include surfactant proteins A and D. SIRPβ (also referred to as CD172b) is expressed on macrophages and neutrophils, however, no known ligands have been reported. SIRPβ contains a short cytoplasmic region in comparison to SIRPα and is known to associate with a signaling component known as DNAX activation protein 12 (DAP12). Thus, SIRPβ is thought to be an activating receptor. SIRPγ (also referred to as CD172g and SIRPβ2) is expressed on lymphocytes and natural killer cells and also binds to CD47, however, no signaling function has been reported as the cytoplasmic tail only contains four amino acids and lacks a sequence that would facilitate association with DAP12. Another member, SIRPδ, has been described and exists as a soluble receptor.

The role of SIRPα, in particular, has been investigated in respect of its inhibitory role in the phagocytosis of host cells by macrophages. For example, CD47 binding to SIRPα on macrophages, triggers inhibitory signals that negatively regulates phagocytosis. Alternatively, positive signaling effects mediated through SIRPα a binding have been reported (Shultz et al., 1995, J Immunol 154, 180-91).

SIRPα Sequences

Exemplary SIRPα sequences for human and mouse are set forth in Table 3. For cDNA sequences, consecutive exons are separated by alternating underlined text. For protein sequences, signal peptides are underlined and transmembrane and cytoplasmic sequences are italicized

TABLE 3

| | |
|---|---|
| mouse SIRPα cDNA NM_007547.3 | GCGCTCGGCCGGGCCGCCCTCGCGCTGGCCTCGCG ACGGCTCCGCACAGCCCGCACTCGCTCTGCGAGCT GTCCCCGCTCGCGCTTGCTCTCCGATCTCCGTCCC CGCTCCCTCTCCCTCTTCCTCTCCCCTCTTTCCT TCTCCCTCGCTATCCGCTCCCCCGCCCCGTGCCT CTGGCTCTGCGCCTGGCTCCCTCGGGTCCGCTCCC CTTTCCCGCCCGGCCTGGCCGGCGTCACGCTCCC |

TABLE 3-continued

```
CGGAGTCTCCCCGCTCGGCGGCGTCTCATTGTGGG
AGGGGGTCAGATCACCCCGCCGGGCGGTGGCGCTG
GGGGGCAGCGGGAGGGGGAGGGGCCTTAGTCGTTC
GCCCGCGCCGCCCGCCCGCCTGCCGAGCGCGCTCA
CCGCCGCTCTCCCTCCTTGCTCTGCAGCCGCGGCC
CATGGAGCCCGCCGGCCCGGCCCCTGGCCGCCTAG
GGCCGCTGCTGCTCTGCCTGCTGCTCTCCGCGTCC
TGTTTCTGTACAGGAGCCACGGGGAAGGAACTGAA
GGTGACTCAGCCTGAGAAATCAGTGTCTGTTGCTG
CTGGGGATTCGACCGTTCTGAACTGCACTTTGACC
TCCTTGTTGCCGGTGGGACCCATTAGGTGGTACAG
AGGAGTAGGGCCAAGCCGGCTGTTGATCTACAGTT
TCGCAGGAGAATACGTTCCTCGAATTAGAAATGTT
TCAGATACTACTAAGAGAAACAATATGGACTTTTC
CATCCGTATCAGTAATGTCACCCCAGCAGATGCTG
GCATCTACTACTGTGTGAAGTTCCAGAAAGGATCA
TCAGAGCCTGACACAGAAATACAATCTGGAGGGGG
AACAGAGGTCTATGTACTCGCCAAACCTTCTCCAC
CGGAGGTATCCGGCCCAGCAGACAGGGGCATACCT
GACCAGAAAGTGAACTTCACCTGCAAGTCTCATGG
CTTCTCTCCCCGGAATATCACCCTGAAGTGGTTCA
AAGATGGGCAAGAACTCCACCCCTTGGAGACCACC
GTGAACCCTAGTGGAAAGAATGTCTCCTACAAGAT
CTCCAGCACAGTCAGGGTGGTACTAAACTCCATGG
ATGTTAATTCTAAGGTCATCTGCGAGGTAGCCCAC
ATCACCTTGGATAGAAGCCCTCTTCGTGGGATTGC
TAACCTGTCTAACTTCATCCGAGTTTCACCCACCC
GTGAAGGTCACCCAACAGTCCCCGACGTCAATGAA
CCAGGTGAACCTCACCTGCCGGGCTGAGAGGTTCT
ACCCCGAGGATCTCCAGCTGATCTGGCTGGAGAAT
GGAAACGTATCACGGAATGACACGCCCAAGAATCT
CACAAAGAACACGGATGGGACCTATAATTACACAA
GCTTGTTCCTGGTGAACTCATCTGCTCATAGAGAG
GACGTGGTGTTCACGTGCCAGGTGAAGCACGACCA
ACAGCCAGCGATCACCCGAAACCATACCGTGCTGG
GATTTGCCCACTCGAGTGATCAAGGGAGCATGCAA
ACCTTCCCTGATAATAATGCTACCCACAACTGGAA
TGTCTTCATCGGTGTGGGCGTGGCGTGTGCTTTGC
TCGTAGTCCTGCTGATGGCTGCTCTCTACCTCCTC
CGGATCAAACAGAAGAAAGCCAAGGGGTCAACATC
TTCCACACGGTTGCACGAGCCCGAGAAGAACGCCA
GGGAAATAACCCAGATCCAGGACACAAATGACATC
AACGACATCACATACGCAGACCTGAATCTGCCCAA
AGAGAAGAAGCCCGCACCCCGGGCCCCTGAGCCTA
ACAACCACACAGAATATGCAAGCATTGAGACAGGC
AAAGTGCCTAGGCCAGAGGATACCCTCACCTATGC
TGACCTGGACATGGTCCACCTCAGCCGGGCACAGC
CAGCCCCCAAGCCTGAGCCATCTTTCTCAGAGTAT
GCTAGTGTCCAGGTCCAGAGGAAGTGAATGGGGCT
GTGGTCTGTACTAGGCCCCATCCCCACAAGTTTTC
TTGTCCTACATGGAGTGGCCATGACGAGGACATCC
AGCCAGCCAATCCTGTCCCCAGAAGGCCAGGTGGC
ACGGGTCCTAGGACCAGGGGTAAGGGTGGCCTTTG
TCTTCCCTCCGTGGCTCTTCAACACCTCTTGGGCA
CCCACGTCCCCTTCTTCCGGAGGCTGGGTGTTGCA
GAACCAGAGGGCGAACTGGAGAAAGCTGCCTGGAA
TCCAAGAAGTGTTGTGCCTCGGCCCATCACTCGTG
GGTCTGGATCCTGGTCTTGGCAACCCCAGGTTGCG
TCCTTGATGTTCCAGAGCTTGGTCTTCTGTGTGGA
GAAGAGCTCACCATCTCTACCCAACTTGAGCTTTG
GGACCAGACTCCCTTTAGATCAAACCGCCCCATCT
GTGGAAGAACTACACCAGAAGTCAGCAAGTTTTCA
GCCAACAGTGCTGGCCTCCCCACCTCCCAGGCTGA
CTAGCCCTGGGGAGAAGGAACCCTCTCCTCCTAGA
CCAGCAGAGACTCCCTGGGCATGTTCAGTGTGGCC
CCACCTCCCTTCCAGTCCCAGCTTGCTTCCTCCAG
CTAGCACTAACTCAGCAGCATCGCTCTGTGGACGC
CTGTAAATTATTGAGAAATGTGAACTGTGCAGTCT
TAAAGCTAAGGTGTTAGAAAATTTGATTTATGCTG
TTTAGTTGTTGTTGGGTTTCTTTTCTTTTTAATTT
CTTTTTCTTTTTTGATTTTTTTCTTTCCCTTAAA
ACAACAGCAGCAGCATCTTGGCTCTTTGTCATGTG
TTGAATGGTTGGGTCTTGTGAAGTCTGAGGTCTAA
CAGTTTATTGTCCTGGAAGGATTTTCTTACAGCAG
AAACAGATTTTTTCAAATTCCCAGAATCCTGAGG
ACCAAGAAGGATCCCTCAGCTGCTACTTCCAGCAC
CCAGCGTCACTGGGACGAACCAGGCCCTGTTCTTA
CAAGGCCACATGGCTGGCCCTTTGCCTCCATGGCT
ACTGTGGTAAGTGCAGCCTTGTCTGACCCAATGCT
GACCTAATGTTGGCCATTCCACATTGAGGGGACAA
```

TABLE 3-continued

```
                  GGTCAGTGATGCCCCCCTTCACTCACAAGCACTTC
                  AGAGGCATGCAGAGAGAAGGGACACTCGGCCAGCT
                  CTCTGAGGTAATCAGTGCAAGGAGGAGTCCGTTTT
                  TTGCCAGCAACCTCAGCAGGATCACACTGGAACA
                  GAACCTGGTCATACCTGTGACAACACAGCTGTGAG
                  CCAGGGCAAACCACCCACTGTCACTGGCTCGAGAG
                  TCTGGGCAGAGGCTCTGACCCTCCACCCTTTAAAC
                  TGGATGCCGGGGCCTGGCTGGGCCCAATGCCAAGT
                  GGTTATGGCAACCCTGACTATCTGGTCTTAACATG
                  TAGCTCAGGAAGTGGAGGCGCTAATGTCCCCAATC
                  CCTGGGGATTCCTGATTCCAGCTATTCATGTAAGC
                  AGAGCCAACCTGCCTATTTCTGTAGGTGCGACTGG
                  GATGTTAGGAGCACAGCAAGGACCCAGCTCTGTAG
                  GGCTGGTGACCTGATACTTCTCATAATGGCATCTA
                  GAAGTTAGGCTGAGTTGGCCTCACTGGCCCAGCAA
                  ACCAGAACTTGTCTTTGTCCGGGCCATGTTCTTGG
                  GCTGTCTTCTAATTCCAAAGGGTTGGTTGGTAAAG
                  CTCCACCCCCTTCTCCTCTGCCTAAAGACATCACA
                  TGTGTATACACACGGGTATAGATGAGTTAAA
                  AGAATGTCCTCGCTGGCATCCTAATTTTGTCTTAA
                  GTTTTTTTGGAGGGGAGAAAGGAACAAGGCAAGGA
                  AGATGTGTAGCTTTGGCTTTAACCAGGCAGCCTGG
                  GGGCTCCCAAGCCTATGGAACCCTGGTACAAAGAA
                  GAGAACAGAAGCGCCCTGTGAGGAGTGGGATTTGT
                  TTTTCTGTAGACCAGATGAGAAGGAAACAGGCCCT
                  GTTTTGTACATAGTTGCAACTTAAAATTTTTGGCT
                  TGCAAAATATTTTTGTAATAAAGATTTCTGGGTAA
                  CAATAAAAAAAAAAAAAAAAAA  (SEQ ID NO: 1)

Mouse SIRPα      MEPAGPAPGRLGPLLLCLLLSASCFCTGATGKELK
Protein          VTQPEKSVSVAAGDSTVLNCTLTSLLPVGPIRWYR
Np_031573.2      GVGPSRLLIYSFAGEYVPRIRNVSDTTKRNNMDFS
                 IRISNVTPADAGIYYCVKFQKGSSEPDTEIQSGGG
                 TEVYVLAKPSPPEVSGPADRGIPDQKVNFTCKSHG
                 FSPRNITLKWFKDGQELHPLETTVNPSGKNVSYNI
                 SSTVRVVLNSMDVNSKVICEVAHITLDRSPLRGIA
                 NLSNFIRVSPTVKVTQQSPTSMNQVNLTCRAERFY
                 PEDLQLIWLENGNVSRNDTPKNLTKNTDGTYNYTS
                 LFLVNSSAHREDVVFTCQVKHDQQPAITRNHTVLG
                 FAHSSDQGSMQTFP*DNNATHNWNVFIGVGVACALL*
                 *VVLLMAALYLLRIKQKKAKGSTSSTRLHEPEKNAR*
                 *EITQIQDTNDINDITYADLNLPKEKKPAPRAPEPN*
                 *NHTEYASIETGKVPRPEDTLTYADLDMVHLSRAQP*
                 *APKPEPSFSEYASVQVQRK*  (SEQ ID NO: 2)

Human SIRPα      TCCGGCCCGCACCCACCCCCAAGAGGGGCCTTCAG
DNA              CTTTGGGGCTCAGAGGCACGACCTCCTGGGGAGGG
NM_001040022.1   TTAAAAGGCAGACGCCCCCCGCCCCCCGCGCCCC
                 CGCGCCCCGACTCCTTCGCCGCCTCCAGCCTCTCG
                 CCAGTGGAAGCGGGGAGGGAGCGCGCGCGGCCGGAG
                 TCCGGAGGCGAGGGAGGTCGGCCGCAACTTCCCC
                 GGTCCACCTTAAGAGGACGATGTAGCCAGCTCGCA
                 GCGCTGACCTTAGAAAAACAAGTTTGCGCAAAGTG
                 GAGCGGGGACCCGGCCTCTGGGCAGCCCCGGCGGC
                 GCTTCCAGTGCCTTCCAGCCCTCGCGGGCGGCGCA
                 GCCGCGGCCCATGGAGCCCGCCGGCCCGGCCCCCG
                 GCCGCCTCGGGCCGCTGCTCTGCCTGCTGCTCGCC
                 GCGTCCTGCTTCTGTCAGGAGTGGCGGGTGAGGA
                 GGAGCTGCAGGTGATTCAGGCCTGACAAGTCCGTGT
                 TGGTTGCAGCTGGAGAGACAGCCACTCTGCGCTGC
                 ACTGCGACCTCTCTGATCCCTGTGGGGCCCATCCA
                 GTGGTTCAGAGGAGCTGGACCAGGCCGGGAATTAA
                 TCTACAATCAAAAGAAGGCCACTTCCCCCGGGTA
                 ACAACTGTTTCAGACCTTCACAAAGAGAAACAACAT
                 GGACTTTTCCATCCGCATCGGTAACATCACCCCAG
                 CAGATGCCGGCACCTACTACTGTGTGAAGTTCCGG
                 AAAGGGAGCCCCGATGACGTGGAGTTTAAGTCTGG
                 CAGCAGGCACTGAGCTGTCTGTGCGCGCCAAACCT
                 CTGCCCCCGTGGTATCGGGCCCTGCGGCGAGGGCC
                 ACACCTCAGCACACAGTGAGCTTCACCTGCGAGTC
                 CCACGGCTTCTCACCCAGAGACATCACCCTGAAAT
                 GGTTCAAAAATGGGAATGAGCTCTCAGACTTCCAG
                 ACCAACGTGGACCCCGTAGGAGAGCGTGTCCTA
                 CAGCATCCACAGCACAGCCAAGGTGGTGCTGACCC
                 GCGAGGACGTTCACTCTGACTCATCTGCGAGGTT
                 GGCCCACGTCACCTTGCAGGGGACCCTCTTCGTG
                 GGACTGCCAACTTGTCTGAGACCATCCGAGTTCCA
                 CCCACCTTGGAGGTTACTCAACAGCCCGTGAGGGC
                 AGAGAACCAGGTGAATGTCACCTGCCAGGTGAGGA
                 AGTTCTACCCCCAGAGACTACAGCTGACCTGGTTG GAGAATGGAAACGTGTCCCGGACAGAAACGGCCTC
                  AACCGTTACAGAGAACAAGGATGGTACCTACAACT
                  GGATGAGCTGGTCCTGGTGAATGTATCTGCCCAC
                  AGGGATGATGTGAAGCTCACCTGCCAGGTGGAGCA
                  TGACGGGCAGCCAGCGGTCAGCAAAAGCCATGACC
                  TGAAGGTCTCAGCCCACCCGAAGGAGCAGGGCTCA
                  AATACCGCCGCTGAGAACACTGGATCTAATGAACG
                  GAACATCTATATTGTGGTGGGTGTGGTGTGCACCT
                  TGCTGGTGGCCCTACTGATGGCGGCCCTCTACCTC
                  GTCCGAATCAGACAGAAGAAAGCCCAGGGCTCCAC
                  TTCTTCTACAAGGTTGCATGAGCCCGAGAAGAATG
                  CCAGAGAAATAACACAGGACACAAATGATATCACA
                  TATGCAGACCTGAACCTGCCCAAGGGGAAGAAGCC
                  TGCTCCCCAGGCTGCGGAGCCCAACAACCACACGG
                  AGTATGCCAGCATTGAGACCAGCCCGCAGCCCGCG
                  TCGGAGGACACCCTCACCTATGCTGACCTGGACAT
                  GGTCCACCTCAACCGGACCCCAAGCAGCCGGCCC
                  CCAAGCCTGAGCCGTCCTTCTCAGAGTACGCCAGC
                  GTCCAGGTCCCGAGGAAGTGAATGGGACCGTGGTT
                  TGCTCTAGCACCCATCTCTACGCGCTTTCTTGTCC
                  CACAGGGAGCCGCCGTGATGAGCACAGCCAACCCA
                  GTTCCCGGAGGGCTGGGGCGGTGCAGGCTCTGGGA
                  CCCAGGGGCAGGGTGGCTCTTCTCTCCCCACCCC
                  TCCTTGGCTCTCCAGCACTTCCTGGGCAGCCACGG
                  CCCCCTCCCCCACATTGCCACATACCTGGAGGCT
                  GACCGTGCCAAACCAGCCAGGGAACCAACCTGGGA
                  AGTGGCCAGAACTGCCTGGGGTCCAAGAACTCTTG
                  TGCCTCCGTCCATCACCATGTGGGTTTTGAAGACC
                  CTCGACTGCCTCCCCGATGCTCCGAAGCCTGATCT
                  TCCAGGGTGGGGAGGAGAAAATCCCACCTCCCCTG
                  ACCTCCACCACCTCCACCACCACCACCACCACCAC
                  CACCACCACTACCACCACCACCCCAACTGGGGCTAG
                  AGTGGGGAAGATTTCCCCTTTAGATCAAACTGCCC
                  CTTCCATGGAAAAGCTGGAAAAAAAACTCTGGAACC
                  CATATCCAGGCTTGGTGAGGTTGCTGCCAACAGTC
                  CTGGCCTCCCCCATCCCTAGGCTAAAGAGCCATGA
                  GTCCTGGAGGAGGAGGACCCCTCCCAAAGGACT
                  GGAGACAAAACCCTCTGCTTCCTTGGGTCCCTCCA
                  AGACTCCCTGGGGCCCAACTGTGTTGCTCCACCCG
                  GACCCATCTCTCCCTTCTAGACCTGAGCTTGCCCC
                  TCCAGCTAGCACTAAGCAACATCTCGCTGTGGACG
                  CCTGTAAATTACTGAGAAATGTGAAACGTGCAATG
                  TTGAAACTGAGGTGTTAGAAAACTTGATCTGTGGT
                  GTTTTGTTTTGTTTTTTTCTTAAAACAACAGCAA
                  CGTGATCTTGGCTGTCTGTCATGTGTTGAAGTCCA
                  TGGTTGGGTCTTTGTGAAGTCTGAGGTTTAACAGTT
                  TGTTGTCCTGGAGGGATTTTCTTACAGCGAAGACT
                  TGAGTTCCTCCAAGTCCCAGAACCCCAAGAATGGG
                  CAAGAAGGATCAGGTCAGCCACTCCCTGGAGACAC
                  AGCCTTCTGGCTGGGACTGACTTGGCCATGTTCTC
                  AGCTGAGCCACGCAGGCTGGTAGTGCAGCCTTCTGT
                  GACCCCGCTGTGGTAAGTCCAGCCTGCCCAGGGCT
                  GCTGAGGGCTGCCTCTTGACAGTGCAGTCTTATCG
                  AGACCCAATGCCTCAGTCTGCTCATCCGTAAAGTG
                  GGGATAGTGAAGATGACACCCCTCCCCACCACCTC
                  TCATAAGCACTTTAGGAACACACAGAGGGTAGGGA
                  TAGTGGCCCTGGCCGTCTATCCTACCCCTTTAGTG
                  ACCGCCCCCATCCCGCTTTCTGAGCTGATCTTTG
                  AAGAAGAAATCTTCCATTTCTGCTCTCAAACCCTA
                  CTGGGATCAAACTGGAATAAATTGAAGACAGCCAG
                  GGGGATGGTGCAGCTGTGAAGCTCGGGCTGATTCC
                  CCCTGTGTCCCAGAAGGTTGGCCAGAGGGTGTGAC
                  CCAGTTACCCTTTAACCCCACCCTTCCAGTCGGG
                  TGTGAGGGCTGACCGGGCCCAGGGCAAGCAGATG
                  TCGCAAGCCCTATTTATTCAGTCTTCACTATAACT
                  CTTAGAGTTGAGACGCTAATGTTCATGACTCCTGG
                  CCTTGGGATGCCCAAGGGATTTCTGGCTCAGGCTG
                  TAAAAGTAGCTGAGCCATCCTGCCCATTCCTGGAG
                  GTCCTACAGGTGAAACTGCAGGAGCTCAGCATAGA
                  CCCAGCTCTCTGGGGGATGGTCACCTGGTGATTTC
                  AATGATGGCATCAGGAATTACTGAGCAACAGA
                  CCATGTGGACAGCTTTGGCAGAGCTCCCGTGTGG
                  CATCTGGGAGCCACAGTGACCCAGCCACCTGGCTC
                  AGGCTAGTTCCAAATTCAAAAGATTGGCTTGTAA
                  ACCTTCGTCTCCCTCTCTTTACCCAGAGACAGCAC
                  ATACGTGTGCACACGCATGCACACACACATTCAGT
                  ATTTTAAAGAATGTTTCTTGGTGCCATTTTCAT
                  TTTATTTTATTTTTTAATTCTTGGAGGGGGAAATA
                  AGGGAATAAGGCCAAGGAAGATGTATAGCTTTAGC
                  TTTAGCCTGGCAACCTGGAGAATCCACATACCTTG
```

TABLE 3-continued

|  |  |
|---|---|
|  | TGTATTGAACCCCAGGAAAAGGAAGAGGTCGAACC<br>AACCCTGCGGAAGGAGCATGGTTTCAGGAGTTTAT<br>TTTAAGACTGCTGGGAAGGAAACAGGCCCCATTTT<br>GTATATAGTTGCAACTTAAACTTTTTGGCTTGCAA<br>AATATTTTTGTAATAAAGATTTCTGGGTAATAATG<br>A (SEQ ID NO: 3) |
| Human SIRPα<br>Protein<br>NP_001035111.1 | MEPAGPAPGRLGPLLCLLLAASCAWSGVAGEEELQ<br>VIQPDKSVLVAAGETATLRCTATSLIPVGPIQWFR<br>GAGPGRELIYNQKEGHFPRVTTVSDLTKRNNMDFS<br>IRIGNITPADAGTYYCVKFRKGSPDDVEFKSGAGT<br>ELSVRAKPSAPVVSGPAARATPQHTVSFTCESHGF<br>SPRDITLKWFKNGNELSDFQTNNTDPVGESVSYSI<br>HSTAKVVLTREDVHSQVICEVAHVTLQGDPLRGTA<br>NLSETIRVPPTLEVTQQPVRAENQVNVTCQVRKFY<br>PQRLQLTWLENGNVSRTETASTVTENKDGTYNWMS<br>WLLVNVSAHRDDVKLTCQVEHDGQPAVSKSHDLKV<br>SAHPKEQGSNTAAENTGSNERNIYIVVGVVCTLLV<br>ALLMAALYLVRIRQKKAQGSTSSTRLHEPEKNARE<br>ITQDTNDITYADLNLPKGKKPAPQAAEPNNHTEYA<br>YSIQTSPQPASEDTLTYADLDMVHLNRTPKQPAPK<br>PEPSFSEASVQVPRK (SEQ ID NO: 4) |
| Humanized<br>SIRPα Protein | MEPAGPAPGRLGPLLLCLLLSASCFCTGVAGEEEL<br>QVIQPDKSVLVAAGETATLRCTATSLIPVGPIQWF<br>RGAGPGRELIYNQKEGHFPRVTTVSDLTKRNNMDF<br>SIRIGNITPADAGTYYCVKFRKGSPDDVEFKSGAG<br>TELSVRAKPSAPVVSGPAARATPQHTVSFTCESHG<br>FSPRDITLKWFKNGNELSDFQTNVDPVGESVSYSI<br>HSTAKVVLTREDVHSQVICEVAHVTLQGDPLRGTA<br>NLSETIRVPPTLEVTQQPVRAENQVNVTCQVRKFY<br>PQRLQLTWLENGNVSRTETASTVTENKDGTYNWMS<br>WLLVNVTSAHRDDVKLTCQVEHDGQPAVTSKSHDL<br>KVSAHPKEQGSNTAADNNATHNWNVFIGVGVACAL<br>KLVVLLMAALYLLRIKQKAKGSTSSTRLHEPEKNA<br>REITQIQDTNDINDITYADLNLPKEKKPAPRAPEP<br>NNHTEYASIETGKVPRPEDTLTYADLDMVHLSRAQ<br>PAPKPEPSFSEYASVQVQRK (SEQ ID NO: 5) |

Humanized SIRPα Non-Human Animals

Non-human animals are provided that express humanized SIRPα proteins on the surface of immune cells (e.g., myeloid cells) of the non-human animals resulting from a genetic modification of an endogenous locus of the non-human animal that encodes a SIRPα protein. Suitable examples described herein include rodents, in particular, mice.

A humanized SIRPα gene, in some embodiments, comprises genetic material from a heterologous species (e.g., humans), wherein the humanized SIRPα gene encodes a SIRPα protein that comprises the encoded portion of the genetic material from the heterologous species. In some embodiments, a humanized SIRPα gene of the present invention comprises genomic DNA of a heterologous species that corresponds to the extracellular portion of a SIRPα protein that is expressed on the plasma membrane of a cell. Non-human animals, embryos, cells and targeting constructs for making non-human animals, non-human embryos, and cells containing said humanized SIRPα gene are also provided.

In some embodiments, an endogenous SIRPα gene is deleted. In some embodiments, an endogenous SIRPα gene is altered, wherein a portion of the endogenous SIRPα gene is replaced with a heterologous sequence (e.g., a human SIRPα sequence in whole or in part). In some embodiments, all or substantially all of an endogenous SIRPα gene is replaced with a heterologous gene (e.g., a human SIRPα gene). In some embodiments, a portion of a heterologous SIRPα gene is inserted into an endogenous non-human SIRPα gene at an endogenous SIRPα locus. In some embodiments, the heterologous gene is a human gene. In some embodiments, the modification or humanization is made to one of the two copies of the endogenous SIRPα gene, giving rise to a non-human animal is heterozygous with respect to the humanized SIRPα gene. In other embodiments, a non-human animal is provided that is homozygous for a humanized SIRPα gene.

A non-human animal of the present invention contains a human SIRPα gene in whole or in part at an endogenous non-human SIRPα locus. Thus, such non-human animals can be described as having a heterologous SIRP gene. The replaced, inserted or modified SIRPα gene at the endogenous SIRPα locus can be detected using a variety of methods including, for example, PCR, Western blot, Southern blot, restriction fragment length polymorphism (RFLP), or a gain or loss of allele assay. In some embodiments, the non-human animal is heterozygous with respect to the humanized SIRPα gene In various embodiments, a humanized SIRPα gene according to the present invention includes a SIRPα gene that has a second, third and fourth exon each having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to a second, third and fourth exon that appear in a human SIRPα gene of Table 3.

In various embodiments, a humanized SIRPα gene according to the present invention includes a SIRPα gene that has a nucleotide coding sequence (e.g., a cDNA sequence) at least 50% (e.g., 50%, 55%, 60%0, 65%, 70%, 75%, 80%, 85%, 90%, 91%, 92%, 93%, 94%, 95%, 96%, 97%, 98%, 99% or more) identical to nucleotides 352-1114 that appear in a human SIRPα cDNA sequence of Table 3.

In various embodiments, a humanized SIRPα protein produced by a non-human animal of the present invention has an extracellular portion having a sequence that is at least 500 (e.g., 50%, 55%, 60%, 65%, 70%, 75%, 80%, 85%, 90%, 91%, 92%, 93%, 94%, 95%, 96%, 97%, 98%, 99% or more) identical to an extracellular portion of a human SIRPα protein that appears in Table 3.

In various embodiments, a humanized SIRPα a protein produced by a non-human animal of the present invention has an extracellular portion having a sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to amino acid residues 28-362 that appear in a human SIRPα protein of Table 3.

In various embodiments, a humanized SIRPα protein produced by a non-human animal of the present invention has an amino acid sequence that is at least 50% (e.g., 50%, 55%, 60%, 65%, 70%, 75%, 80%, 85%, 90%, 91%, 92%, 93%, 94%, 95%, 96%, 97%, 98%, 99% or more) identical to an amino acid sequence of a humanized SIRPα protein that appears in Table 3.

Compositions and methods for making non-human animals that expresses a humanized SIRPα protein, including specific polymorphic forms or allelic variants (e.g., single amino acid differences), are provided, including compositions and methods for making non-human animals that expresses such proteins from a human promoter and a human regulatory sequence. In some embodiments, compositions and methods for making non-human animals that expresses such proteins from an endogenous promoter and an endogenous regulatory sequence are also provided. The methods include inserting the genetic material encoding a human SIRPα protein in whole or in part at a precise location in the genome of a non-human animal that corresponds to an endogenous SIRPα gene thereby creating a humanized SIRPα gene that expresses a SIRPα protein that is human in whole or in part. In some embodiments, the methods include inserting genomic DNA corresponding to exons 2-4 of a human SIRPα gene into an endogenous SIRPα gene of the non-human animal thereby creating a humanized gene that encodes a SIRPα protein that contains a human portion containing amino acids encoded by the inserted exons.

A humanized SIRPα gene approach employs a relatively minimal modification of the endogenous gene and results in natural SIRPα-mediated signal transduction in the non-human animal, in various embodiments, because the genomic sequence of the SIRPα sequences are modified in a single fragment and therefore retain normal functionality by including necessary regulatory sequences. Thus, in such embodiments, the SIRPα gene modification does not affect other surrounding genes or other endogenous SIRP genes. Further, in various embodiments, the modification does not affect the assembly of a functional receptor on the plasma and maintains normal effector functions via binding and subsequent signal transduction through the cytoplasmic portion of the receptor which is unaffected by the modification.

A schematic illustration (not to scale) of an endogenous murine SIRPα gene and a humanized SIRPα gene is provided in FIG. 1. As illustrated, genomic DNA containing exons 2-4 of a human SIRPα gene is inserted into an endogenous murine SIRPα gene locus by a targeting construct. This genomic DNA includes comprises the portion of the gene that encodes an extracellular portion (e.g., amino acid resides 28-362) of a human SIRPα protein responsible for ligand binding.

A non-human animal (e.g., a mouse) having a humanized SIRPα gene at the endogenous SIRPα locus can be made by any method known in the art. For example, a targeting vector can be made that introduces a human SIRPα gene in whole or in part with a selectable marker gene. FIG. 1 illustrates a mouse genome comprising an insertion of exons 2-4 of a human SIRPα. As illustrated, the targeting construct contains a 5' homology arm containing sequence upstream of exon 2 of an endogenous murine SIRPα gene, followed by a genomic DNA fragment containing exons 2-4 of a human SIRPα gene, a drug selection cassette (e.g., a neomycin resistance gene flanked on both sides by loxP sequences), and a 3' homology arm containing sequence downstream of exons 4 of an endogenous murine SIRPα gene. Upon homologous recombination, exons 2-4 of an endogenous murine SIRPα gene is replaced by the sequence contained in the targeting vector. A humanized SIRPα gene is created resulting in a cell or non-human animal that expresses a humanized SIRPα protein that contains amino acids encoded by exons 2-4 of a human SIRPα gene. The drug selection cassette may optionally be removed by the subsequent addition of a recombinase (e.g., by Cre treatment).

In addition to mice having humanized SIRPα genes as described herein, also provided herein are other genetically modified non-human animals that comprise humanized SIRPα genes. In some embodiments, such non-human animals comprise a humanized SIRPα gene operably linked to an endogenous SIRPα promoter. In some embodiments, such non-human animals express a humanized SIRPα protein from an endogenous locus, wherein the humanized SIRPα protein comprises amino acid residues 28-362 of a human SIRPα protein.

Such non-human animals may be selected from the group consisting of a mouse, rat, rabbit, pig, bovine (e.g., cow, bull, buffalo), deer, sheep, goat, chicken, cat, dog, ferret, primate (e.g., marmoset, rhesus monkey). For the non-human animals where suitable genetically modifiable ES cells are not readily available, other methods are employed to make a non-human animal comprising genetic modifications as described herein. Such methods include, e.g., modifying a non-ES cell genome (e.g., a fibroblast or an induced pluripotent cell) and employing nuclear transfer to transfer the modified genome to a suitable cell, e.g., an oocyte, and gestating the modified cell (e.g., the modified oocyte) in a non-human animal under suitable conditions to form an embryo.

In some embodiments, a non-human animal of the present invention is a mammal. In some embodiments, a non-human animal of the present invention is a small mammal, e.g., of the superfamily Dipodoidea or Muroidea. In some embodiments, a genetically modified animal of the present invention is a rodent. In some embodiments, a rodent of the present invention is selected from a mouse, a rat, and a hamster. In some embodiments, a rodent of the present invention is selected from the superfamily Muroidea. In some embodiments, a genetically modified animal of the present invention is from a family selected from Calomyscidae (e.g., mouse-like hamsters), Cricetidae (e.g., hamster, New World rats and mice, voles), Muridae (true mice and rats, gerbils, spiny mice, crested rats), Nesomyidae (climbing mice, rock mice, with-tailed rats, Malagasy rats and mice), Platacanthomyidae (e.g., spiny dormice), and Spalacidae (e.g., mole rates, bamboo rats, and zokors). In some certain embodiments, a genetically modified rodent of the present invention is selected from a true mouse or rat (family Muridae), a gerbil, a spiny mouse, and a crested rat. In some certain embodiments, a genetically modified mouse of the present invention is from a member of the family Muridae. In some embodiment, an non-human animal of the present invention is a rodent. In some certain embodiments, a rodent of the present invention is selected from a mouse and a rat. In some embodiments, a non-human animal of the present invention is a mouse.

In some embodiments, a non-human animal of the present invention is a rodent that is a mouse of a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In some certain embodiments, a mouse of the present invention is a 129 strain selected from the group consisting of a strain that is 129P1, 129P2, 129P3, 129X1, 129S1 (e.g., 129S1/SV, 129S1/SvIm), 129S2, 129S4, 129S5, 129S9/SvEvH, 129/SvJae, 129S6 (129/SvEvTac), 129S7, 129S8, 129T1, 129T2 (see, e.g., Festing et al., 1999, Mammalian Genome 10:836; Auerbach et al., 2000, Biotechniques 29(5):1024-1028, 1030, 1032). In some certain embodiments, a genetically modified mouse of the present invention is a mix of an aforementioned 129 strain and an aforementioned C57BL/6 strain. In some certain embodiments, a mouse of the present invention is a mix of aforementioned 129 strains, or a mix of aforementioned BU6 strains. In some certain embodiments, a 129 strain of the mix as described herein is a 129S6 (129/SvEvTac) strain. In some embodiments, a mouse of the present invention is a BALB strain, e.g., BALB/c strain. In some embodiments, a mouse of the present invention is a mix of a BALB strain and another aforementioned strain.

In some embodiments, a non-human animal of the present invention is a rat. In some certain embodiments, a rat of the present invention is selected from a Wistar rat, an LEA strain, a Sprague Dawley strain, a Fischer strain, F344, F6, and Dark Agouti. In some certain embodiments, a rat strain as described herein is a mix of two or more strains selected from the group consisting of Wistar, LEA, Sprague Dawley, Fischer, F344, F6, and Dark Agouti.

Methods Employing Non-Human Animals Having Humanized SIRPα Genes

SIRPα mutant and transgenic non-human animals (e.g., mice) have been reported (Inagaki et al., 2000, EMBO Journal 19(24):6721-6731; Strowig et al., 2011, Proc. Nat. Acad. Sci. 108(32): 13218-13223). Such animals have been employed in a variety of assays to determine the molecular aspects of SIRPα expression, function and regulation. However, they are not without limitation. For example, use of SIRPα mutant mice have been limited due to deleterious health conditions resulting from an inability of cells containing the mutant form of SIRPα to signal. Further, because CD47, a ligand for SIRPα, might be present on the same cell as the mutant form of SIRPα and both proteins are capable of providing intracellular signals, it is not possible to distinguish if such results are from lack of SIRPα signaling or lack of CD47 binding. In the case of human SIRPα transgenic mice, mouse SIRPα is intact and functional. Thus, SIRPα-dependent functions in various biological processes (e.g., engraftment) cannot be clearly attributed to either human SIRPα or mouse SIRPα function alone in these mice as both the human and mouse SIRPα receptors are present and functional.

Non-human animals of the present invention provide an improved in vivo system and source of biological materials (e.g., cells) expressing human SIRPα that are useful for a variety of assays. In various embodiments, non-human animals of the present invention are used to develop therapeutics that target SIRPα and/or modulate SIRPα-CD47 signaling. In various embodiments, mice of the present invention are used to screen and develop candidate therapeutics (e.g., antibodies) that bind to human SIRPα. In various embodiments, non-human animals of the present invention are used to determine the binding profile of antagonists and/or agonists a humanized SIRPα on the surface of a cell of a non-human animal as described herein.

In various embodiments, non-human animals of the present invention are used to measure the therapeutic effect of blocking or modulating SIRPα signal transduction (e.g., phosphorylation) and the effect on gene expression as a result of cellular changes. In various embodiments, a non-human animal of the present invention of cells isolated therefrom are exposed to a candidate therapeutic that binds to a human SIRPα on the surface of a cell of the non-human animal and, after a subsequent period of time, analyzed for effects on SIRPα-dependent processes, for example, B and/or T cell proliferation, clearance of platelets, and induction of cytokine expression.

Non-human animals of the present invention express humanized SIRPα protein, thus cells, cell lines, and cell cultures can be generated to serve as a source of humanized SIRPα for use in binding and functional assays, e.g., to assay for binding or function of a SIRPα antagonist or agonist, particularly where the antagonist or agonist is specific for a human SIRPα sequence or epitope. In various embodiments, a humanized SIRPα protein expressed by a non-human animal as described herein may comprise a variant amino acid sequence. Variant human SIRPα proteins having variations associated with ligand binding residues have been reported. In various embodiments, non-human animals of the present invention express a humanized SIRPα protein variant. In various embodiments, the variant is polymorphic at an amino acid position associated with ligand binding. In various embodiments, non-human animals of the present invention are used to determine the effect of ligand binding through interaction with a polymorphic variant of human SIRPα.

Cells from non-human animals of the present invention can be isolated and used on an ad hoc basis, or can be maintained in culture for many generations. In various embodiments, cells from a non-human animal of the present invention are immortalized and maintained in culture indefinitely (e.g., in serial cultures).

In various embodiments, cells of non-human animals of the present invention are used in a cell migration or spreading assay to screen and develop candidate therapeutics that modulate human SIRPα. Such processes are necessary for many cellular processes including wound healing, differentiation, proliferation and survival.

In various embodiments, cells of non-human animals of the present invention are used in clonal assays for megakaryocytic colony-forming cells for testing the pharmacotoxicological aspects of candidate therapeutics that target human SIRPα.

In various embodiments, cells of non-human animals of the present invention are used in phagocytosis assays to determine the therapeutic potential of compounds or biological agents to modulate SIRPα-dependent regulation of phagocytosis.

Non-human animals of the present invention provide an in vivo system for the analysis and testing of a drug or vaccine. In various embodiments, a candidate drug or vaccine may be delivered to one or more non-human animals of the present invention, followed by monitoring of the non-human animals to determine one or more of the immune response to the drug or vaccine, the safety profile of the drug or vaccine, or the effect on a disease or condition. Such drugs or vaccines may be improved and/or developed in such non-human animals.

Non-human animals of the present invention provide improved in vio system elucidating mechanisms of human cell-to-cell interaction through adoptive transfer. In various embodiments, non-human animals of the present invention may by implanted with a tumor xenograft, followed by a second implantation of tumor infiltrating lymphocytes could be implanted in the non-human animals by adoptive transfer to determine the effectiveness in eradication of solid tumors or other malignancies. Such experiments may be done with human cells due to the exclusive presence of human SIRPα without competition with endogenous SIRPα of the non-human animal. Further, therapies and pharmaceuticals for use in xenotransplantation can be improved and/or developed in such non-human animals.

Non-human animals of the present invention provide an improved in vivo system for maintenance and development of human hematopoietic stem cells through engraftment. In various embodiments, non-human animals of the present invention provide improved development and maintenance of human stem cells within the non-human animal. In various embodiments, increased populations of differentiated human B and T cells are observed in the blood, bone marrow, spleen and thymus of the non-human animal. In various embodiments, non-human animals of the present invention provide an increase in the level of engraftment of human cells as compared to non-human animals that express both mouse and human SIRPα.

Non-human animals of the present invention can be employed to assess the efficacy of a therapeutic drug targeting human cells. In various embodiments, a non-human animal of the present invention is transplanted with human cells, and a drug candidate targeting such human cells is administered to such animal. The therapeutic efficacy of the drug is then determined by monitoring the human cells in the non-human animal after the administration of the drug.

Drugs that can be tested in the non-human animals include both small molecule compounds, i.e., compounds of molecular weights of less than 1500 kD, 1200 kD, 1000 kD, or 800 dalton, and large molecular compounds (such as proteins, e.g., antibodies), which have intended therapeutic effects for the treatment of human diseases and conditions by targeting (e.g., binding to and/or acting on) human cells.

In some embodiments, the drug is an anti-cancer drug, and the human cells are cancer cells, which can be cells of a primary cancer or cells of cell lines established from a primary cancer. In these embodiments, a non-human animal of the present invention is transplanted with human cancer cells, and an anti-cancer drug is given to the non-human animal. The efficacy of the drug can be determined by assessing whether growth or metastasis of the human cancer cells in the non-human animal is inhibited as a result of the administration of the drug.

In specific embodiments, the anti-cancer drug is an antibody molecule which binds to an antigen on human cancer cells. In particular embodiments, the anti-cancer drug is a bispecific antibody that binds to an antigen on human cancer cells, and to an antigen on other human cells, for example, cells of the human immune system (or "human immune cells") such as B cells and T cells.

In some embodiments, a non-human animal of the present invention is engrafted with human immune cells or cells that differentiate into human immune cells. Such non-human animal with engrafted human immune cells is transplanted with human cancer cells, and is administered with an anti-cancer drug, such as a bispecific antibody that binds to an antigen on human cancer cells and to an antigen on human immune cells (e.g., T-cells). The therapeutic efficacy of the bispecific antibody can be evaluated based on its ability to inhibit growth or metastasis of the human cancer cells in the non-human animal. In a specific embodiment, the non-human animal of the present invention is engrafted with human CD34+ hematopoietic progenitor cells which give rise to human immune cells (including T cells, B cells, NK cells, among others). Human B cell lymphoma cells (e.g., Raji cells) are transplanted into such non-human animal with engrafted human immune cells, which is then administered with a bispecific antibody that binds to CD20 (an antigen on normal B cells and certain B cell malignancies) and to the CD3 subunit of the T-cell receptor, to test the ability of the bispecific antibody to inhibit tumor growth in the non-human animal.

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric.

Example 1. Humanization of an Endogenous Signal-Regulatory Protein (SIRP) Gene

This example illustrates exemplary methods of humanizing an endogenous gene encoding signal-regulatory protein alpha (SIRPα) in a non-human mammal such as a rodent (e.g., a mouse). Human SIRPα is known to exist in at least 10 allelic forms. The methods described in this example can be employed to humanize an endogenous SIRPα gene of a non-human animal using any human allele, or combination of human alleles (or allele fragments) as desired. In this example, human SIRPα variant 1 is employed for humanizing an endogenous SIRPα gene of a mouse.

A targeting vector for humanization of an extracellular region of a SIRP (e.g., SIRPα) gene was constructed using VELOCIGENE® technology (see, e.g., U.S. Pat. No. 6,586,251 and Valenzuela et al. (2003) High-throughput engineering of the mouse genome coupled with high-resolution expression analysis, Nature Biotech. 21(6):652-659).

Briefly, mouse bacterial artificial chromosome (BAC) clone bMQ-261H14 was modified to delete the sequence containing exons 2 to 4 of an endogenous SIRPα gene and insert exons 2 to 4 of a human SIRPα gene using human BAC clone CTD-3035H21. The genomic DNA corresponding to exons 2 to 4 of an endogenous SIRPα gene (~8555 bp) was replaced in BAC clone bMQ-261H14 with a ~8581 bp DNA fragment containing exons 2 to 4 of a human SIRPα gene from BAC clone CTD-3035H21. Sequence analysis of the human SIRPα allele contained in BAC clone CTD-3035H21 revealed the allele to correspond to human variant 1. A neomycin cassette flanked by loxP sites was added to the end of the ~8581 bp human DNA fragment containing exons 2 to 4 of the human SIRPα gene (FIG. 1).

Upstream and downstream homology arms were obtained from mouse BAC DNA at positions 5' and 3' of exons 2 and 4, respectively, and added to the ~8581 bp human fragment-neomycin cassette to create the final targeting vector for humanization of an endogenous SIRPα gene, which contained from 5' to 3' a 5' homology arm containing 19 kb of mouse DNA 5' of exon 2 of the endogenous SIRPα gene, a ~8581 bp DNA fragment containing exons 2 to 4 of a human SIRPα gene, a neomycin cassette flanked by loxP sites, and a 3' homology arm containing 21 kb of mouse DNA 3' of exon 4 of an endogenous SIRPα gene. Targeted insertion of the targeting vector positioned the neomycin cassette in the fifth intron of a mouse SIRPα gene between exons 4 and 5. The targeting vector was linearized by digesting with SwaI and then used in homologous recombination in bacterial cells to achieve a targeted replacement of exons 2 to 4 in a mouse SIRPα gene with exons 2 to 4 of a human SIRPα gene (FIG. 1).

The targeted BAC DNA (described above) was used to electroporate mouse ES cells to created modified ES cells comprising a replacement of exons 2 to 4 in an endogenous mouse SIRPα gene with a genomic fragment comprising exons 2 to 4 of a human SIRPα gene. Positive ES cells containing a genomic fragment comprising exons 2 to 4 of a human SIRPα gene were identified by quantitative PCR using TAQMAN™ probes (Lie and Petropoulos, 1998. Curr. Opin. Biotechnology 9:43-48). The nucleotide sequence across the upstream insertion point included the following, which indicates endogenous mouse sequence upstream of the insertion point (contained within the parentheses below) linked contiguously to a human SIRPα genomic sequence present at the insertion point: (AGCTCTCCTA CCACTAGACT GCTGAGACCC GCTGCTCTGC TCAGGACTCG ATTTCCAGTA CACAATCTCC CTCTTTGAAA AGTACCACAC ATCCTGGGGT) GCTCTTGCAT TTGTGTGACA CTTTGCTAGC CAGGCTCAGT CCTGGGTTCC AGGTGGGGAC TCAAACACAC TGGCACGAGT CTACATTGGA TATTCTTGGT (SEQ ID NO: 6). The nucleotide sequence across the downstream insertion point at the 5' end of the neomycin cassette included the following, which indicates human SIRPα genomic sequence contiguous with cassette sequence downstream of the insertion point (contained within the parentheses below with loxP sequence italicized): GCTCCC-CATT CCTCACTGGC CCAGCCCCTC TTCCCTACTC TTTCTAGCCC CTGCCTCATC TCCCTGGCTG CCAT-
TGGGAG CCTGCCCCAC TGGAAGCCAG (TCGAG
ATAACTTCGTA TAA TGTA TGCTATACGAA G TTAT
ATGCATGGCC TCCGCGCCGG GTTTTGGCGC
CTCCCGCGGG CGCCCCCCTC CTCACGGCGA) (SEQ
ID NO: 7). The nucleotide sequence across the downstream
insertion point at the 3' end of the neomycin cassette
included the following, which indicates cassette sequence
contiguous with mouse genomic sequence 3' of exon 4 of an
endogenous SIRPα a gene (contained within the parentheses
below): CATTCTCAGT ATTGTTTTGC CAAGTTCTAA
TTCCATCAGA CCTCGACCTG CAGCCCCTAG
ATAACTTCGT ATAATGTATG CTATACGAAG
TTATGCTAGC (TGTCTCATAG AGGCTGGCGA
TCTGGCTCAG GGACAGCCAG TACTGCAAAG
AGTATCCTTG TTCATACCTT CTCCTAGTGG
CCATCTCCCT GGGACAGTCA) (SEQ ID NO: 8). Posi-
tive ES cell clones were then used to implant female mice
using the VELOCIMOUSE® method (see, e.g., U.S. Pat.
No. 7,294,754 and Poueymirou et al. 2007, F0 generation
mice that are essentially fully derived from the donor
gene-targeted ES cells allowing immediate phenotypic
analyses Nature Biotech. 25(1):91-99) to generate a litter of
pups containing an insertion of exons 2 to 4 of a human
SIRPα gene into an endogenous SIRPα gene of a mouse.

Targeted ES cells described above were used as donor ES
cells and introduced into an 8-cell stage mouse embryo by
the VELOCIMOUSE® method (supra). Mice bearing the
humanization of exons 2 to 4 of an endogenous SIRPα gene
were identified by genotyping using a modification of allele
assay (Valenzuela et al., supra) that detected the presence of
the human SIRPα gene sequences.

Mice bearing the humanized SIRPα gene construct (i.e.,
containing human SIRPα exons 2 to 4 in a mouse SIRPα
gene) can be bred to a Cre deletor mouse strain (see, e.g.,
International Patent Application Publication No. WO 2009/
114400) in order to remove any loxed neomycin cassette
introduced by the targeting vector that is not removed, e.g.,
at the ES cell stage or in the embryo. Optionally, the
neomycin cassette is retained in the mice.

Pups are genotyped and a pup heterozygous for the
humanized SIRPα gene construct is selected for character-
ization.

Example 2. Expression of Humanized SIRPα in Non-Human Animals

This example illustrates the characteristic expression of
SIRPα protein on the surface of cells from non-human
animals engineered to contain an humanized SIRPα gene
construct as described in Example 1 at an endogenous
SIRPα locus.

Briefly, spleens were isolated from wild type (WT) and
mice heterozygous for a humanized SIRPα gene. Spleens
were then perfused with Collagenase D (Roche Bioscience)
and erythrocytes were lysed with ACK lysis buffer accord-
ing to manufacturer's specifications. Cell surface expression
of mouse and human SIRPα was analyzed by FACS using
fluorochrome-conjugated anti-CD3 (17A2), anti-CD19
(1D3), anti-CD1 b (M1/70), anti-human SIRPα (SE5A5),
and anti-mouse SIRPα (P84). Flow cytometry was per-
formed using BD LSRFORTESSA™. Exemplary expres-
sion of human and mouse SIRPα as detected on the surface
of CD11b+ monocytes is shown in FIG. 2.

Figure 2:
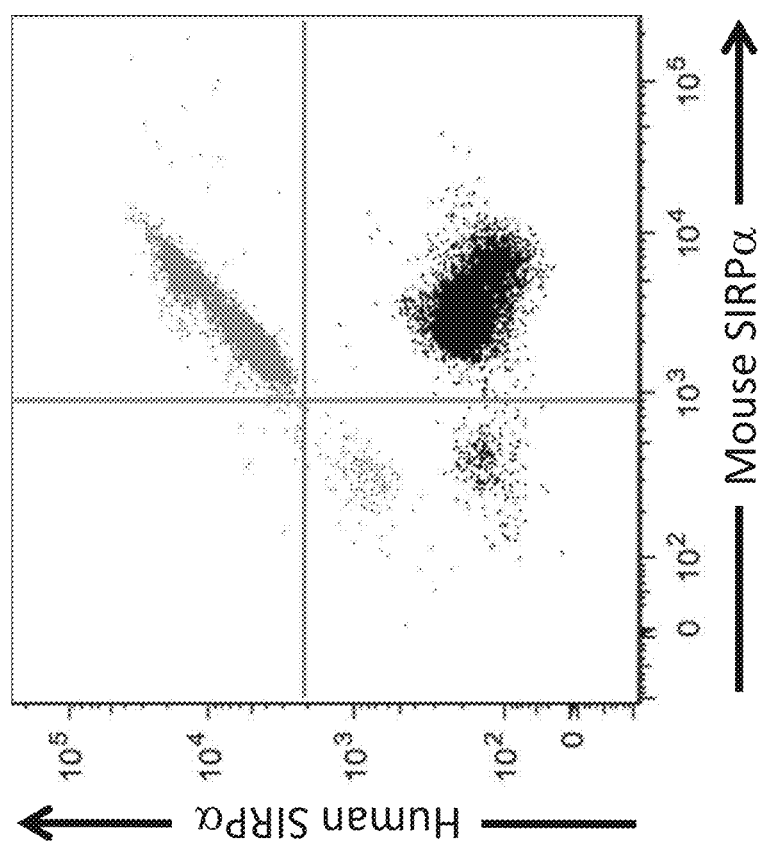
FIG. 2 shows an overlay of SIRPα expression of wild type and mice heterozygous for a humanized SIRPα gene.

As shown in FIG. 2, expression of both mouse and
humanized SIRPα were clearly detectable on the surface of
CD11b+ monocytes from heterozygous mice.

Example 3. Human Cell Engraftment in Humanized SIRP Non-Human Animals

This example illustrates an improved engraftment of
human hematopoietic stem cells in non-human animals of
the present invention having a humanized SIRPα gene.

Briefly, Rag2 KO IL2Rγ$^{null}$ mice with or without a
humanized SIRPα gene were raised under pathogen-free
conditions. Newborn mice (2 to 5 days old) were irradiated
with 240 cGy and injected intra-hepatically with 1×10$^5$
CD34+ human hematopoietic stem cells. The mice were bled
10 to 12 weeks post engraftment and blood was analyzed by
FACS using fluorochrome-conjugated anti-human CD45
(HI30), anti-human CD3 (SK7), anti-human CD19 (HIB19)
and anti-mouse CD45 (30-F11) to check for the reconstitu-
tion of the human immune system. The genetic background
of the mice is BALB/Ta×129/SvJae.

Figure 3:
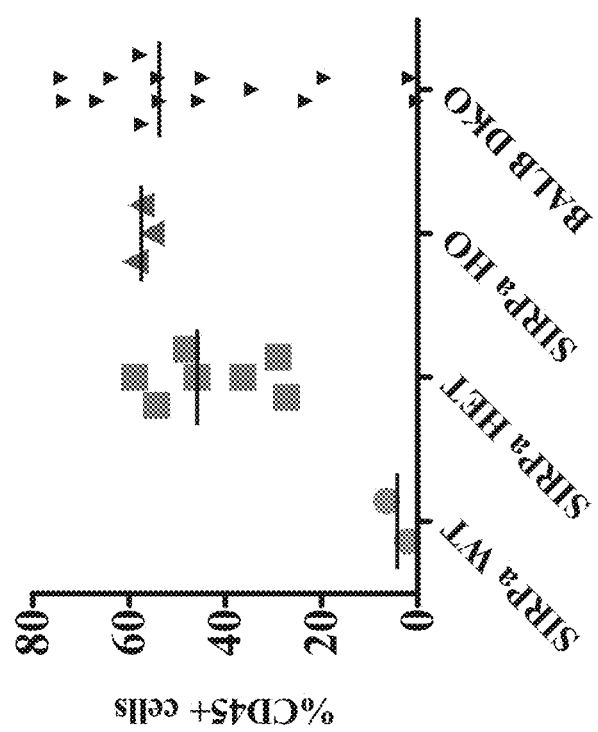
FIG. 3 shows the percent of CD45+ cells in different strains of mice engrafted with human CD34+ cells.
Figure 4:
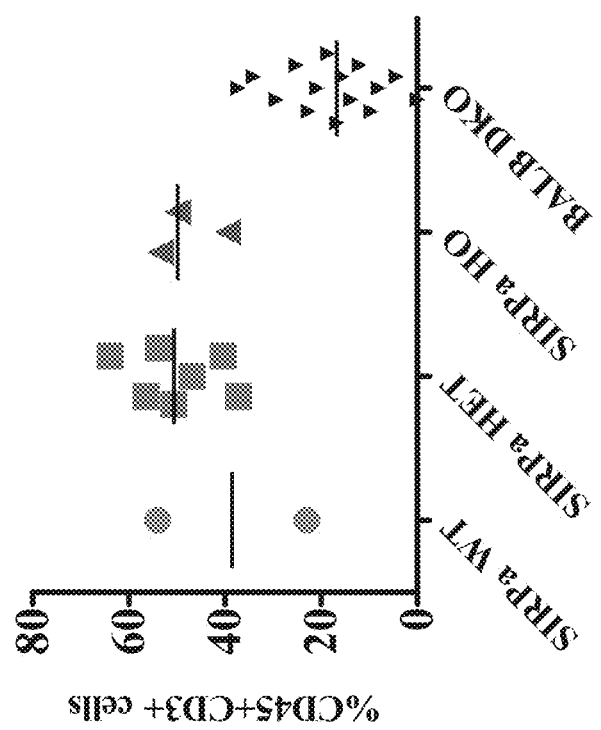
FIG. 4 shows the percent of CD45+CD3$^+$ cells in different strains of mice engrafted with human CD34 cells.
Figure 5:
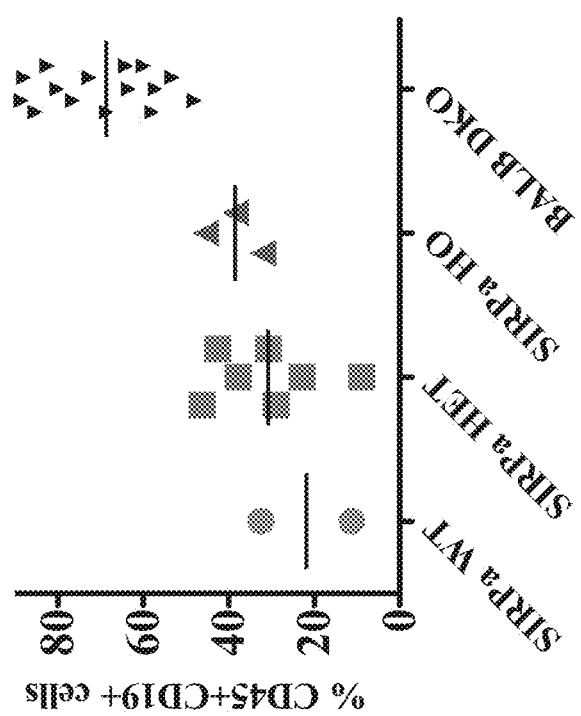
FIG. 5 shows the percent of CD45+CD19$^+$ cells in different strains of mice engrafted with human CD34+ cells.

Exemplary percentages of human CD34 cells in wild
type, mice heterozygous for humanized SIRPα t, mice
homozygous for humanized SIRPα and BALB-Rag2$^{-/-}$
IL2Rγc$^{-/-}$ (DKO) mice are shown in FIGS. 3-5.

As shown in this example, mice homozygous for a
humanized SIRPα gene demonstrate improved engraftment
of human CD34+ cells by providing the highest percentage
of human CD34+ cells in the periphery (e.g., blood) as
compared to other strains tested.

Taken together, these data demonstrate that humanized
SIRPα is functional in the mice as described herein through
expression on the surface of cells in the mouse and begin
capable of supporting the engraftment of human CD34+
hematopoietic stem cells.

Example 4. Evaluating the Efficacy of Ab 1 on Raji Lymphoma Tumor Growth in BRG Mice Summary Ab 1 is bispecific antibody (bsAb) that binds to CD3, a T
cell antigen associated with the T cell receptor (TCR)
complex, and CD20, a B cell surface antigen present on
normal B cells and several B cell lineage malignancies. Ab
1 is designed to bridge CD20-expressing cells with cytotoxic
T cells by binding to the CD3 subunit of the TCR, resulting
in CD20-directed polyclonal T cell killing. CD20 is a
clinically validated target for immunotherapy; the chimeric
antibody rituximab is approved for treatment of Non Hodg-
kin Lymphomas (NHL) and Chronic Lymphocytic Leuke-
mia (CLL). Although patients may become refractory to
rituximab, loss of expression of CD20 is not typically
observed. Therefore, a bispecific antibody bridging CD20-
positive tumor cells with cytotoxic T cells represents a
potential anti-tumor strategy.

In this study, the effect of treatment with CD20×CD3
bsAb Ab 1 on human B cell lymphoma (Raji) tumor growth
was examined in a mouse tumor model. The model utilized
hCD34+ engrafted BALB/c-Rag2null IL2rγnull (BRG)
mice that were humanized for SIRPα. These mice, with
human T, B, and NK cells, as well as granulocytes, mono-
cytes, and dendritic cells (DCs), were treated with Ab 1
twice weekly, resulting in significant suppression of Raji
tumor growth compared to vehicle control and the non-
binding control mAb, Control Ab 5. Ab 1 treatment sup-
pressed tumor growth at both 0.4 mg/kg and 0.04 mg/kg
with greater significance than the vehicle control group throughout the treatment period (p<0.0001). No significant weight loss was observed in any treatment group. These results show that Ab 1 targets Raji tumors in mice with human immune cells, resulting in significant tumor suppression.

Materials and Methods

Materials

Test Compound and Control Antibody

Test compound: Ab 1.

Control antibody: Control Ab 5.

Reagents

TABLE 4

Reagent List

| Reagent | Source | Identification |
|---|---|---|
| Raji cells | Regeneron core facility | Raji P 1-4-10 Passage #4 |
| Human CD34+ hematopoietic stem cells (HSC) isolated from human fetal livers | Advanced Biosciences Resource, Inc. | |
| hPBMCs | Reachbio | Catalog #0500-300, Lot #130322 |
| L-Histidine | Amresco | Catalog #181164-100G, Lot #3363E344 |
| Sucrose | Biosolutions | Catalog #BIO640-07, Lot #0816012 |
| RPMI | Irvine Scientific | Catalog #9160, Lot #9160100803 |
| FBS | Tissue Culture Biologicals | Catalog #101, Lot #107062 |
| Penicillin/ Streptomycin/ L-Glutamine | Gibco | Catalog #10376-016, Lot #1411480 |
| 2-Mercaptoethanol | Gibco | Catalog #21985-023, Lot #762405 |
| Anti-human CD45 | Invitrogen | Catalog #MHCD4518, Clone H130 |
| Anti-human NKp46 | BD Biosciences | Catalog #558051, Catalog 9E2 |
| Anti-human CD19 | BD Biosciences | Catalog #555412, Clone HIB19 |
| Anti-human CD3 | Invitrogen | Catalog #MHCD0328, Clone S4.1 |
| Anti-human CD14 | BD Biosciences | Catalog #557742, Clone M5E2 |
| Anti-human CD45 | BD Biosciences | Catalog #557659, Clone 30-F11 |
| BD Fortessa | BD Biosciences | Special Order Instrument |

Test Systems

The tumor studies presented in this report employed 24-32 week old male and female BALB/c-Rag2null IL2rγnull (BRG) immunodeficient mice humanized for the signal regulatory protein alpha (SIRPα) gene. These were generated at Regeneron by embryonic stem (ES) cell targeting (Strowig et al., Proc Natl Acad Sci USA, 108(32): 13218-13223 (2011)). Upon recognition of CD47, SIRPα inhibits clearance of CD47 positive cells by macrophages. Previous studies have shown that BRG mice expressing the human SIRPα transgene have enhanced engraftment of human HSC (Strowig et al., Proc Natl Acad Sci USA, 108(32): 13218-13223 (2011)).

Newborn SIRPα BRG pups were irradiated and engrafted with hCD34+ hematopoietic progenitor cells derived from fetal liver (Traggiai, et al., Science, 304(5667): 104-107 (2004)). These human HSCs give rise to human T, B, and NK cells, as well as granulocytes, monocytes, and dendritic cells (DCs). Due to the low levels of circulating human B cells, there are low levels of circulating human IgG. Furthermore, these mice do not develop germinal centers, lack lymph nodes and have limited T and B cell replenishment if these cells are depleted. Murine monocytes, DCs, and granulocytes remain present as well. Immune cell composition was confirmed by flow cytometry of blood, and mice were randomized by % human CD45 engraftment prior to use in tumor studies. Mice were implanted with Raji tumor cells at Day 0, and the ability of Ab 1 to block tumor growth over 4 weeks was tested. Body weights and tumor volumes were recorded on days 3, 6, 9, 13, 16, 20, 23, 27, 30 and 34 following implantation.

Experimental Design

Reconstitution of Human Immune System in SIRPα BRG Mice

Immunodeficient BALB/c Rag2/-yc-/- (BRG) human SIRP alpha (SIRPα BRG) mice were bred in the germ-free isolators in the Regeneron animal facility. Neonate mice were irradiated with one dose of 300 cGrey, 8-24 h prior to injection of human CD34+ hematopoietic stem cells (HSC) isolated from human fetal livers. The engraftment was allowed to develop for 12-16 weeks and the number of engrafted cells was periodically evaluated by flow cytometry. For the entire duration of the experiment, animals were housed in the Regeneron animal facility under standard conditions in a 12-hour day/night rhythm with access to food and water ad libitum. The number of animals per cage was limited to a maximum of 5 mice.

Mouse blood was analyzed to determine percent engraftment levels prior to initiating the study. Whole blood was collected into two capillary tubes containing 150 uL of 2% EDTA (ethylenediaminetetraacetic acid; 15 mg/mL). Red blood cells were lysed using ACK lysing buffer for 3 minutes and the buffer was neutralized with PBS (no calcium or magnesium). Cells were blocked with Fc Block for 5 minutes at 4° C. and then stained with human CD45, NKp46, CD19, CD3 and CD14 for 30 minutes at 4° C. Samples were analyzed by 5-laser flow cytometry (BD Fortessa). Percent engraftment was determined as the % human CD45+ cells of total cells.

Raji Tumor Study Procedure in SIRPα BRG Mice

On day 0, groups of 5 SIRPα BRG mice were administered $2 \times 10^6$ Raji tumor cells subcutaneously. On the same day, mice were treated with an intraperitoneal (IP) dose of either Ab 1 (0.4 or 0.04 mg/kg), non-binding control mAb Control Ab 5 (which binds a feline antigen with no cross-reactivity to human CD20 or CD3) at a dose of 0.4 mg/kg or vehicle alone. Mice subsequently received two doses of antibody/week for 4 weeks. Tumor growth was measured with calipers on days 3, 6, 9, 13, 16, 20, 23, 27, 30 and 34. Study groups are summarized in Table 5.

TABLE 5

Summary of Treatment Groups in SIRPα BRG Mice

| Groups | Tumor | Antibody | Dose (mg/kg) | Route | Schedule | # Mice |
|---|---|---|---|---|---|---|
| Control Groups | Raji | No antibody (Vehicle alone) | 0 | IP | 2x/wk | 5 |
| | Raji | Control Ab 5 | 0.4 | IP | 2x/wk | 5 |
| Experimental Groups | Raji | Ab 1 | 0.4 | IP | 2x/wk | 5 |
| | Raji | Ab 1 | 0.04 | IP | 2x/wk | 5 |

Specific Procedures

Preparation of Reagents

Ab 1 and Control Ab 5 were each diluted to the desired concentration in Vehicle (10 mM histidine, 5% sucrose, pH 5.8). Raji cells were obtained from the Regeneron core facility (passage 4) and maintained in culture media: RPMI 1640+10% FBS+ Pen Strep-L-Glu+Mercaptoethanol. Raji cells were diluted to the desired concentration in media.

Statistical Analyses

Statistical analyses were performed utilizing GraphPad software Prism 5.0 (MacIntosh Version). Statistical significance was determined by two-way ANOVA with Tukey's multiple comparisons post-test. Data from each of the readouts were compared across treatment groups. A threshold of $p<0.05$ was considered statistically significant, as indicated by *. Mice that died prior to the end of study were removed from the combined tumor growth curve (but not the individual mouse growth curve) graphs as indicated and statistical analysis in order to analyze by two-way ANOVA.

Results

Ab 1 Suppresses Raji Tumor Cell Growth in hCD34+ Engrafted SIRPα BRG Mice

Figure 6:
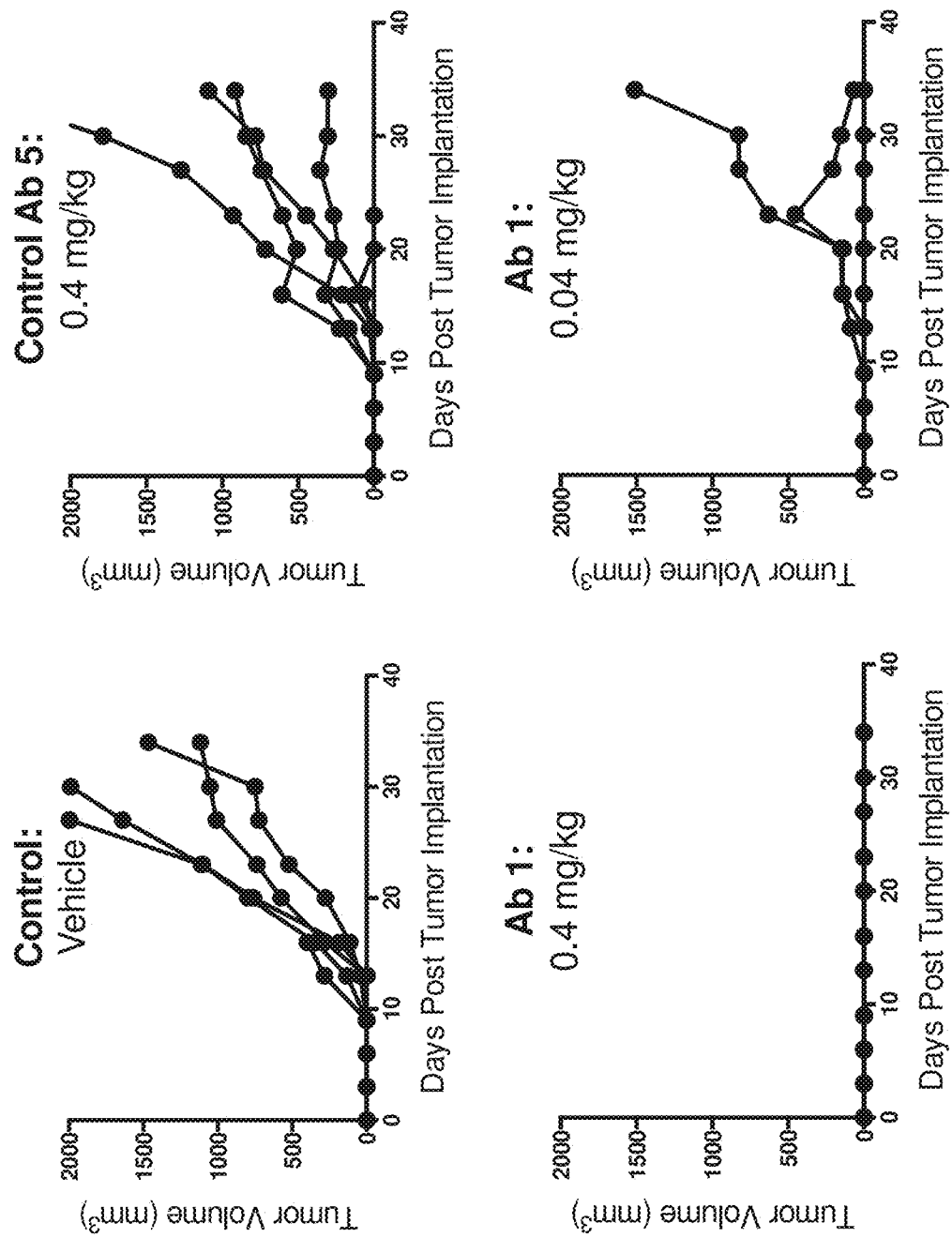
FIG. 6 shows that Ab 1 suppressed growth of Raji tumors in a dose-dependent manner in hCD34+ engrafted SIRPα BRG mice. Raji tumor volume was measured on days 3, 6, 9, 13, 16, 20, 23, 27, 30 and 34 post tumor implantation. Data for individual animals (Panels A-D) is presented. hCD34+ engrafted SIRPα BRG mice were administered $2\times10^6$ Raji tumor cells subcutaneously on Day 0. Control groups received no antibody (vehicle control) (Panel A). For experimental groups, on Day 0 mice were treated with an IP dose of a non-binding control Ab (control Ab 5) at 0.4 mg/kg (Panel B), or Ab 1 at 0.4 mg/kg (Panel C) or 0.04 mg/kg (Panel D), followed by twice weekly doses for the length of the study. The composite data for all individual test groups are shown in FIG. 7.

Ab 1 suppressed Raji tumor growth compared to vehicle control and non-binding control in hCD34+ engrafted SIRPα BRG mice (FIG. 6). Newborn SIRPα BRG pups were irradiated and engrafted with hCD34+ fetal liver cells as hematopoietic progenitor cells (Traggiai, et al., Science, 304(5667): 104-107 (2004)), which gave rise to human T, B, and NK cells, as well as granulocytes, monocytes, and DCs. On day 0, hCD34+ engrafted SIRPα BRG mice were administered $2 \times 10^6$ Raji tumor cells subcutaneously. On the same day, mice were treated with an intraperitoneal (IP) dose of either Ab 1 (0.4 or 0.04 mg/kg) or the non-binding control mAb Control Ab 5, or vehicle control, followed by twice weekly doses throughout the study.

Figure 7:
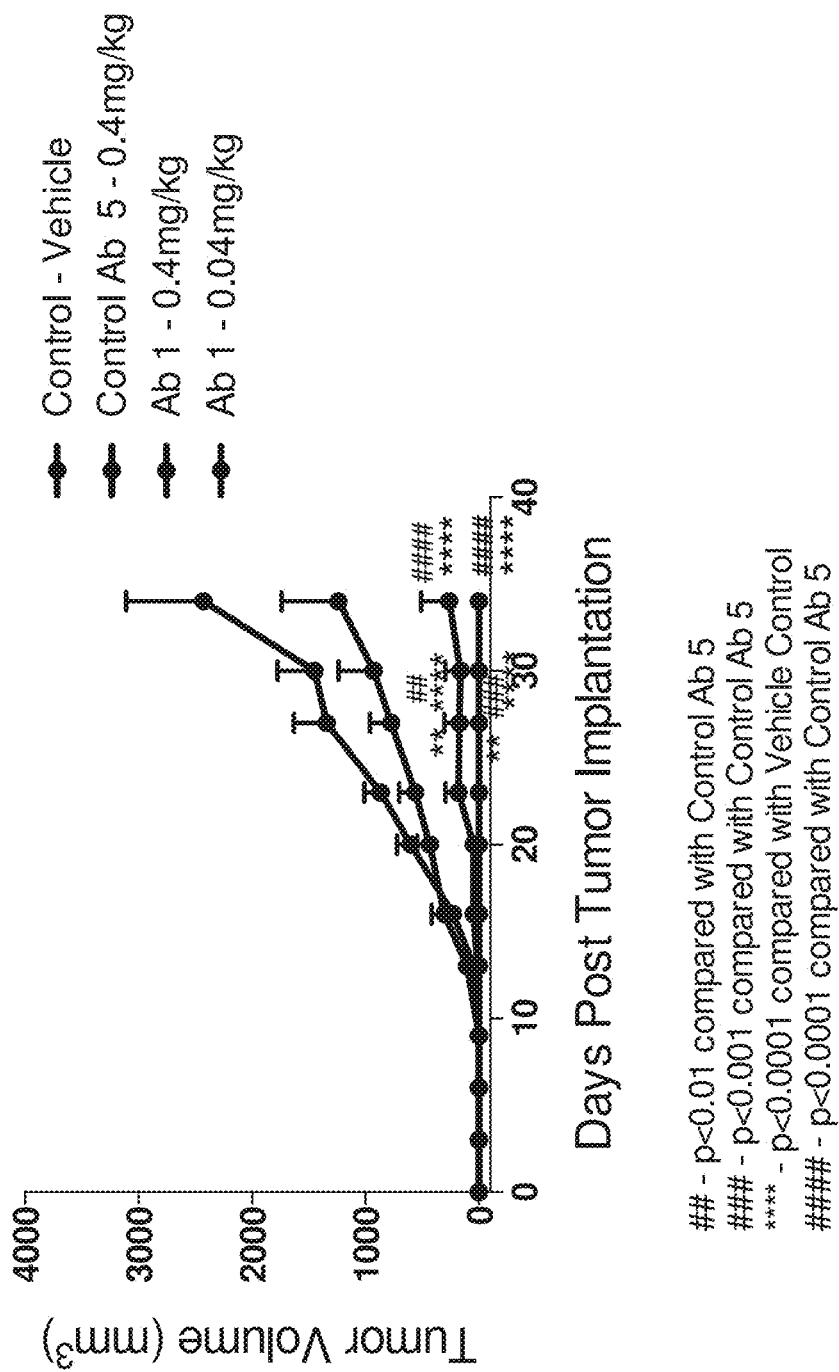
FIG. 7 shows that Ab 1 significantly suppressed growth of Raji tumors compared to controls in hCD34+ engrafted SIRPα BRG mice. Data represents the composite data from n=4-5 mice per group as shown in FIG. 6. Data are expressed as mean (SEM) and were analyzed using analysis of variance (ANOVA) and post hoc tests to probe significant effects (Tukey's for two-way ANOVA). One mouse in the vehicle control group, Control Ab 5 group, and Ab 1 0.4 mg/kg group was excluded from this composite graph due to early death in order to analyze data by two-way ANOVA.
Figure 8:
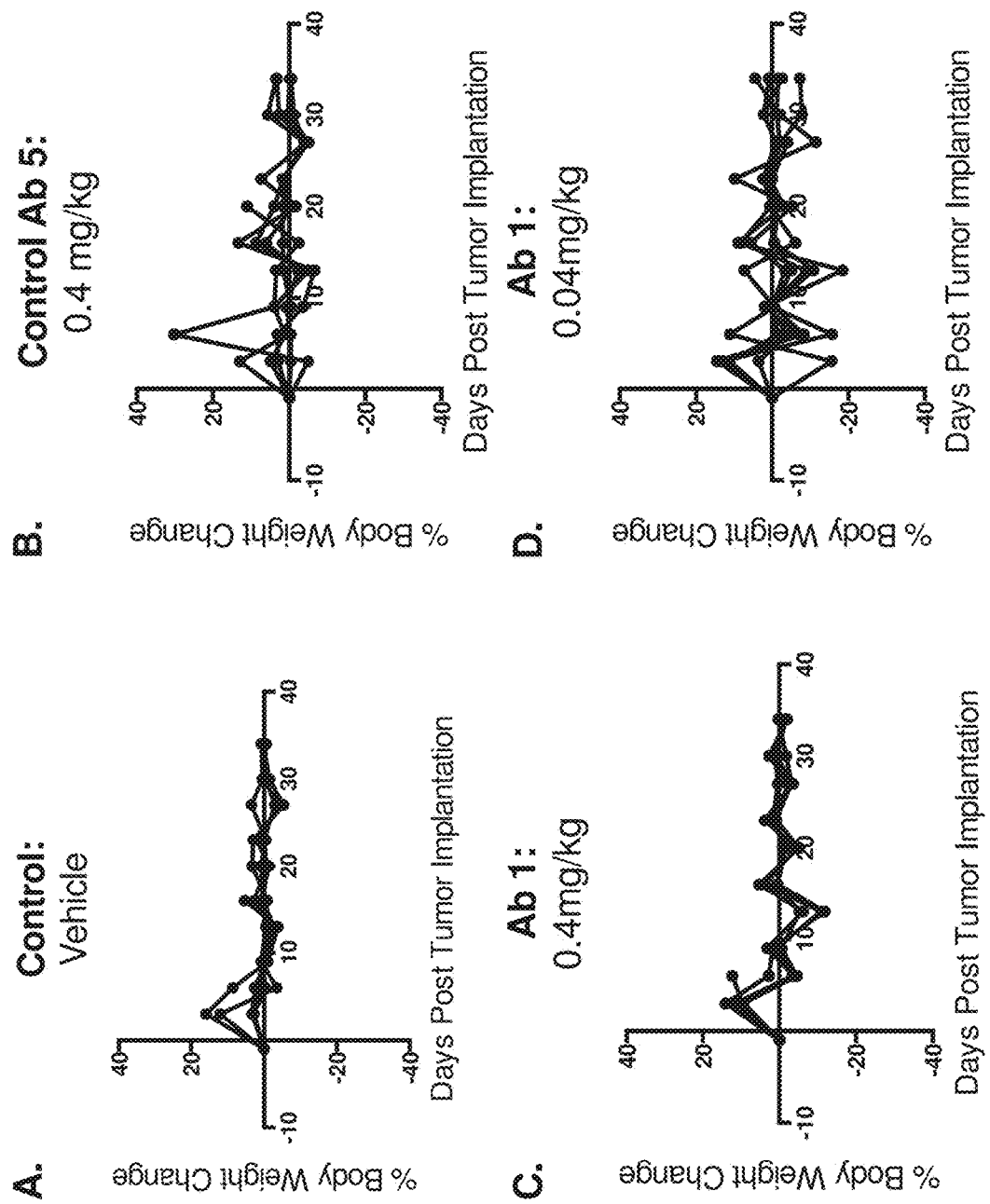
FIG. 8 shows that Ab 1 did not affect body weight in hCD34+ engrafted SIRPα BRG mice. Body weights were measured on days 3, 6, 9, 13, 16, 20, 23, 27, 30 and 34 post tumor implantation. Data for individual animals (Panels A-D) was measured. hCD34+ engrafted SIRPα BRG mice were administered $2\times10^6$ Raji tumor cells subcutaneously on Day 0. Control groups received no antibody (vehicle control) (Panel A). For experimental groups, on Day 0 mice were treated with an IP dose of the IgG1 non-binding Control Ab 5 at 0.4 mg/kg (Panel B) or Ab 1 at 0.4 mg/kg (Panel C) or 0.04 mg/kg (Panel D), followed by twice weekly doses for the length of the study.

Compared to the vehicle control groups and the non-binding control groups, Ab 1 significantly suppressed Raji tumor outgrowth administered at doses of 0.04 mg/kg ($p<0.0001$) or 0.4 mg/kg ($p<0.0001$) on day 34 post tumor implantation (FIG. 7). Furthermore, the effects of Ab 1 treatment were dose-dependent, with 0.4 mg/kg Ab 1 suppressing growth completely throughout the study, as compared to 0.04 mg/kg Ab 1, which suppressed tumor growth completely by Day 30. Neither Ab 1 nor the non-binding control mAb had a significant effect on mouse body weight throughout the study (FIG. 8).

CONCLUSION

The effect of treatment with Ab1, a CD20×CD3 bsAb, on Raji tumor growth was examined in a mouse model. Ab 1 was effective in tumor growth suppression in hCD34+ engrafted SIRPα BRG mice with human T, B, and NK cells, as well as granulocytes, monocytes, and DCs. Twice weekly treatment with Ab 1 resulted in significant and dose-dependent suppression of Raji human B cell lymphoma tumor growth compared to vehicle control and non-binding control. No significant weight loss was observed in any treatment group. These results show that Ab 1 targets Raji tumors in mice with human immune cells, resulting in significant tumor growth suppression.

EQUIVALENTS

Having thus described several aspects of at least one embodiment of this invention, it is to be appreciated by those skilled in the art that various alterations, modifications, and improvements will readily occur to those skilled in the art. Such alterations, modifications, and improvements are intended to be part of this disclosure, and are intended to be within the spirit and scope of the invention. Accordingly, the foregoing description and drawing are by way of example only and the invention is described in detail by the claims that follow.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification.

Those skilled in the art will appreciate typical standards of deviation or error attributable to values obtained in assays or other processes described herein.

The publications, websites and other reference materials referenced herein to describe the background of the invention and to provide additional detail regarding its practice are hereby incorporated by reference.

We claim:

1. A method of making a rat, comprising
   a) modifying an endogenous rat SIRPα locus in a rat ES cell such that the modified SIRPα locus comprises a humanized SIRPα gene, wherein the humanized SIRPα gene
      (i) comprises exon 1 of a rat SIRPα gene, exons 2, 3 and 4 of a human SIRPα gene, and exons 5, 6, 7 and 8 of the rat SIRPα gene,
      (ii) is operably linked to a rat SIRPα promoter at the endogenous rat SIRPα locus, and
      (iii) encodes a humanized SIRPα protein comprising an extracellular portion of the human SIRPα protein encoded by the human SIRPα gene and an intracellular portion of the rat SIRPα protein encoded by the rat SIRPα gene;
   b) obtaining a rat ES cell comprising the modified SIRPα locus; and
   c) generating a rat using the rat ES cell of step (b), wherein the rat generated is homozygous for the humanized SIRPα gene.

2. The method of claim 1, wherein the extracellular portion of the human SIRPα protein comprises amino acid residues 28-362 of the human SIRPα protein.

3. The method of claim 1, wherein the human SIRPα protein comprises the amino acid sequence as set forth in SEQ ID NO: 4.

4. The method of claim 1, wherein the rodent does not express an endogenous rodent SIRPα protein.

5. A method of engrafting human cells into a rat, comprising the steps of:
   (a) providing a rat whose genome comprises a humanized SIRPα gene at an endogenous rat SIRPα locus, wherein the humanized SIRPα gene
      (i) comprises exon 1 of a rat SIRPα gene, exons 2, 3 and 4 of a human SIRPα gene, and exons 5, 6, 7 and 8 of the rat SIRPα gene,
      (ii) is operably linked to a rat SIRPα promoter at the endogenous rat SIRPα locus, and
      (iii) expresses in the rat a humanized SIRPα protein comprising an extracellular portion of the human SIRPα protein encoded by the human SIRPα gene and an intracellular portion of the rat SIRPα protein encoded by the rat SIRPα gene; and
      wherein the rat is homozygous for the humanized SIRPα gene; and
   (b) transplanting one or more human cells into the rat.

6. The method of claim 5, wherein the human cells are hematopoietic stem cells.

7. The method of claim 5, wherein the human cells are transplanted intravenously, intraperitoneally, or subcutaneously.

8. A method of assessing the therapeutic efficacy of a drug targeting human cells, comprising:
   (a) providing a rat whose genome comprises a humanized SIRPα gene at an endogenous rat SIRPα locus, wherein the humanized SIRPα gene
      (i) comprises exon 1 of a rat SIRPα gene, exons 2, 3 and 4 of a human SIRPα gene, and exons 5, 6, 7 and 8 of the rat SIRPα gene,
      (ii) is operably linked to a rat SIRPα promoter at the endogenous rat SIRPα locus, and
      (iii) expresses in the rat a humanized SIRPα protein comprising an extracellular portion of the human SIRPα protein encoded by the human SIRPα gene and an intracellular portion of the rat SIRPα protein encoded by the rat SIRPα gene; and
      wherein the rat is homozygous for the humanized SIRPα gene;
   (b) transplanting one or more human cells into the rat;
   (c) administering a drug candidate to the rat; and
   (d) monitoring the human cells in the rat to assess the therapeutic efficacy of the drug candidate.

9. The method of claim 8, wherein the human cells are human cancer cells, and the drug candidate is an anti-cancer drug candidate.

10. The method of claim 9, wherein the human cancer cells are monitored to determine whether growth or metastasis of the human cancer cells in the rat is inhibited by the drug candidate.

11. The method of claim 8, wherein the drug candidate is an antibody.

12. The method of claim 8, wherein the rat further comprises human immune cells.

13. The method of claim 12, wherein the transplanted human cells are human cancer cells and the drug candidate is a bispecific antibody that binds to an antigen on the human immune cells and an antigen on the transplanted human cancer cells.

14. The method of claim 13, wherein the human cancer cells are monitored to determine whether growth or metastasis of the human cancer cells in the rat is inhibited by the drug candidate.

\* \* \* \* \*

SEQUENCE LISTING

<160> NUMBER OF SEQ ID NOS: 8

<210> SEQ ID NO 1
<211> LENGTH: 4007

```
<212> TYPE: DNA
<213> ORGANISM: Mus musculus

<400> SEQUENCE: 1
gcgctcggcc gggccgccct cgcgctggcc tcgcgacggc tccgcacagc ccgcactcgc      60
tctgcgagct gtcccgctc gcgcttgctc tccgatctcc gtcccgctc cctctccctc      120 ttcctctccc cctctttcct tctccctcgc tatccgctcc ccgccccg tgcctctggc      180 tctgcgcctg gctccctcgg gtccgctccc ctttccgcc ggcctggccc ggcgtcacgc      240
tcccggagtc tccccgctcg gcggcgtctc attgtgggag ggggtcagat caccccgccg      300
ggcggtggcg ctgggggca gcggaggggg aggggcctta gtcgttcgcc cgcgccgccc      360
gcccgcctgc cgagcgcgct caccgccgct ctccctcctt gctctgcagc gcgggccat      420 ggagcccgcc ggcccggccc ctggccgcct agggccgctg ctgctctgcc tgctgctctc      480
cgcgtcctgt ttctgtacag gagccacggg gaaggaactg aaggtgactc agcctgagaa      540
atcagtgtct gttgctgctg gggattcgac cgttctgaac tgcactttga cctccttgtt      600
gccggtggga cccattaggt ggtacagagg agtagggcca agccggctgt tgatctacag      660
tttcgcagga gaatacgttc ctcgaattag aaatgtttca gatactacta agagaaacaa      720
tatggacttt tccatccgta tcagtaatgt caccccagca gatgctggca tctactactg      780
tgtgaagttc cagaaaggat catcagagcc tgacacagaa atacaatctg gagggggaac      840
agaggtctat gtactcgcca aaccttctcc accggaggta tccggcccag cagacagggg      900
catacctgac cagaaagtga acttcacctg caagtctcat ggcttctctc cccggaatat      960
caccctgaag tggttcaaag atgggcaaga actccacccc ttggagacca ccgtgaaccc      1020
tagtggaaag aatgtctcct acaacatctc cagcacagtc agggtggtac taaactccat      1080
ggatgttaat tctaaggtca tctgcgaggt agcccacatc accttggata aagccctct      1140 tcgtgggatt gctaacctgt ctaacttcat ccgagtttca cccaccgtga aggtcaccca      1200
acagtccccg acgtcaatga accaggtgaa cctcacctgc cgggctgaga ggttctaccc      1260
cgaggatctc cagctgatct ggctggaaaa tggaaacgta tcacggaatg acacgcccaa      1320
gaatctcaca aagaacacgg atgggaccta taattacaca agcttgttcc tggtgaactc      1380
atctgctcat agagaggacg tggtgttcac gtgccaggtg aagcacgacc aacagccagc      1440
gatcacccga aaccataccg tgctgggatt tgcccactcg agtgatcaag ggagcatgca      1500
aaccttccct gataataatg ctacccacaa ctggaatgtc ttcatcggtg tgggcgtggc      1560
gtgtgctttg ctcgtagtcc tgctgatggc tgctctctac ctcctccgga tcaaacagaa      1620
gaaagccaag gggtcaacat cttccacacg gttgcacgag cccgagaaga acgccaggga      1680
aataacccag atccaggaca caaatgacat caacgcacatc acatacgcag acctgaatct      1740
gcccaaagag aagaagcccg cacccccgggc cctgagcct aacaaccaca cagaatatgc      1800
aagcattgag acaggcaaag tgcctaggcc agaggatacc ctcacctatg ctgacctgga      1860
catggtccac ctcagccggg cacagccagc ccccaagcct gagccatctt tctcagagta      1920
tgctagtgtc caggtccaga ggaagtgaat ggggctgtgg tctgtactag gccccatccc      1980
cacaagtttt cttgtcctac atggagtggc catgacgagg acatccagcc agccaatcct      2040
gtccccagaa ggccaggtgg cacgggtcct aggaccaggg gtaagggtgg cctttgtctt      2100
ccctccgtgg ctcttcaaca cctcttgggc acccacgtcc ccttcttccg gaggctgggt      2160
gttgcagaac cagagggcga actggagaaa gctgcctgga atccaagaag tgttgtgcct      2220
```

-continued

| | | | | | |
|---|---|---|---|---|---|
| cggcccatca | ctcgtgggtc | tggatcctgg | tcttggcaac | cccaggttgc | gtccttgatg | 2280 |
| ttccagagct | tggtcttctg | tgtggagaag | agctcaccat | ctctacccaa | cttgagcttt | 2340 |
| gggaccagac | tccctttaga | tcaaaccgcc | ccatctgtgg | aagaactaca | ccagaagtca | 2400 |
| gcaagttttc | agccaacagt | gctggcctcc | ccacctccca | ggctgactag | ccctggggag | 2460 |
| aaggaaccct | ctcctcctag | accagcagag | actccctggg | catgttcagt | gtggccccac | 2520 |
| ctcccttcca | gtcccagctt | gcttcctcca | gctagcacta | actcagcagc | atcgctctgt | 2580 |
| ggacgcctgt | aaattattga | gaaatgtgaa | ctgtgcagtc | ttaaagctaa | ggtgttagaa | 2640 |
| aatttgattt | atgctgttta | gttgttgttg | ggtttctttt | cttttttaatt | tcttttctt | 2700 |
| ttttgatttt | ttttctttcc | cttaaaacaa | cagcagcagc | atcttggctc | tttgtcatgt | 2760 |
| gttgaatggt | tgggtcttgt | gaagtctgag | gtctaacagt | ttattgtcct | ggaaggattt | 2820 |
| tcttacagca | gaaacagatt | ttttttcaaat | tcccagaatc | ctgaggacca | agaaggatcc | 2880 |
| ctcagctgct | acttccagca | cccagcgtca | ctgggacgaa | ccaggccctg | ttcttacaag | 2940 |
| gccacatggc | tggccctttg | cctccatggc | tactgtggta | agtgcagcct | tgtctgaccc | 3000 |
| aatgctgacc | taatgttggc | cattccacat | tgagggggaca | aggtcagtga | tgccccccctt | 3060 |
| cactcacaag | cacttcagag | gcatgcagag | agaagggaca | ctcggccagc | tctctgaggt | 3120 |
| aatcagtgca | aggaggagtc | cgttttttgc | cagcaaacct | cagcaggatc | acactggaac | 3180 |
| agaacctggt | catacctgtg | acaacacagc | tgtgagccag | gcaaaccac | ccactgtcac | 3240 |
| tggctcgaga | gtctgggcag | aggctctgac | cctccaccct | ttaaactgga | tgccggggcc | 3300 |
| tggctgggcc | caatgccaag | tggttatggc | aaccctgact | atctggtctt | aacatgtagc | 3360 |
| tcaggaagtg | gaggcgctaa | tgtccccaat | ccctggggat | tcctgattcc | agctattcat | 3420 |
| gtaagcagag | ccaacctgcc | tatttctgta | ggtgcgactg | ggatgttagg | agcacagcaa | 3480 |
| ggacccagct | ctgtagggct | ggtgacctga | tacttctcat | aatggcatct | agaagttagg | 3540 |
| ctgagttggc | ctcactggcc | cagcaaacca | gaacttgtct | ttgtccggc | catgttcttg | 3600 |
| ggctgtcttc | taattccaaa | gggttggttg | gtaaagctcc | accccttct | cctctgccta | 3660 |
| aagacatcac | atgtgtatac | acacacgggt | gtatagatga | gttaaaagaa | tgtcctcgct | 3720 |
| ggcatcctaa | ttttgtctta | agtttttttg | gagggagaaa | ggaacaaggc | aagggaagat | 3780 |
| gtgtagcttt | ggctttaacc | aggcagcctg | ggggctccca | agcctatgga | accctggtac | 3840 |
| aaagaagaga | acagaagcgc | cctgtgagga | gtgggatttg | tttttctgta | gaccagatga | 3900 |
| gaaggaaaca | ggccctgttt | tgtacatagt | tgcaacttaa | aattttttggc | ttgcaaaata | 3960 |
| ttttttgtaat | aaagatttct | gggtaacaat | aaaaaaaaaa | aaaaaaa | | 4007 |

<210> SEQ ID NO 2
<211> LENGTH: 509
<212> TYPE: PRT
<213> ORGANISM: Mus musculus

<400> SEQUENCE: 2

Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Ala Thr Gly Lys
            20                  25                  30

Glu Leu Lys Val Thr Gln Pro Glu Lys Ser Val Ser Val Ala Ala Gly
        35                  40                  45

Asp Ser Thr Val Leu Asn Cys Thr Leu Thr Ser Leu Leu Pro Val Gly
    50                  55                  60

```
Pro Ile Arg Trp Tyr Arg Gly Val Gly Pro Ser Arg Leu Leu Ile Tyr
 65                  70                  75                  80

Ser Phe Ala Gly Glu Tyr Val Pro Arg Ile Arg Asn Val Ser Asp Thr
                 85                  90                  95

Thr Lys Arg Asn Asn Met Asp Phe Ser Ile Arg Ile Ser Asn Val Thr
                100                 105                 110

Pro Ala Asp Ala Gly Ile Tyr Tyr Cys Val Lys Phe Gln Lys Gly Ser
                115                 120                 125

Ser Glu Pro Asp Thr Glu Ile Gln Ser Gly Gly Thr Glu Val Tyr
130                 135                 140

Val Leu Ala Lys Pro Ser Pro Glu Val Ser Gly Pro Ala Asp Arg
145                 150                 155                 160

Gly Ile Pro Asp Gln Lys Val Asn Phe Thr Cys Lys Ser His Gly Phe
                165                 170                 175

Ser Pro Arg Asn Ile Thr Leu Lys Trp Phe Lys Asp Gly Gln Glu Leu
                180                 185                 190

His Pro Leu Glu Thr Thr Val Asn Pro Ser Gly Lys Asn Val Ser Tyr
                195                 200                 205

Asn Ile Ser Ser Thr Val Arg Val Val Leu Asn Ser Met Asp Val Asn
210                 215                 220

Ser Lys Val Ile Cys Glu Val Ala His Ile Thr Leu Asp Arg Ser Pro
225                 230                 235                 240

Leu Arg Gly Ile Ala Asn Leu Ser Asn Phe Ile Arg Val Ser Pro Thr
                245                 250                 255

Val Lys Val Thr Gln Gln Ser Pro Thr Ser Met Asn Gln Val Asn Leu
                260                 265                 270

Thr Cys Arg Ala Glu Arg Phe Tyr Pro Glu Asp Leu Gln Leu Ile Trp
                275                 280                 285

Leu Glu Asn Gly Asn Val Ser Arg Asn Asp Thr Pro Lys Asn Leu Thr
                290                 295                 300

Lys Asn Thr Asp Gly Thr Tyr Asn Tyr Thr Ser Leu Phe Leu Val Asn
305                 310                 315                 320

Ser Ser Ala His Arg Glu Asp Val Val Phe Thr Cys Gln Val Lys His
                325                 330                 335

Asp Gln Gln Pro Ala Ile Thr Arg Asn His Thr Val Leu Gly Phe Ala
                340                 345                 350

His Ser Ser Asp Gln Gly Ser Met Gln Thr Phe Pro Asp Asn Asn Ala
                355                 360                 365

Thr His Asn Trp Asn Val Phe Ile Gly Val Gly Val Ala Cys Ala Leu
                370                 375                 380

Leu Val Val Leu Leu Met Ala Ala Leu Tyr Leu Leu Arg Ile Lys Gln
385                 390                 395                 400

Lys Lys Ala Lys Gly Ser Thr Ser Ser Thr Arg Leu His Glu Pro Glu
                405                 410                 415

Lys Asn Ala Arg Glu Ile Thr Gln Ile Gln Asp Thr Asn Asp Ile Asn
                420                 425                 430

Asp Ile Thr Tyr Ala Asp Leu Asn Leu Pro Lys Glu Lys Lys Pro Ala
                435                 440                 445

Pro Arg Ala Pro Glu Pro Asn Asn His Thr Glu Tyr Ala Ser Ile Glu
                450                 455                 460

Thr Gly Lys Val Pro Arg Pro Glu Asp Thr Leu Thr Tyr Ala Asp Leu
465                 470                 475                 480
```

```
          Asp Met Val His Leu Ser Arg Ala Gln Pro Ala Pro Lys Pro Glu Pro
                          485                 490                 495

Ser Phe Ser Glu Tyr Ala Ser Val Gln Val Gln Arg Lys
                  500                 505

<210> SEQ ID NO 3
<211> LENGTH: 4201
<212> TYPE: DNA
<213> ORGANISM: Homo sapiens

<400> SEQUENCE: 3
tccggcccgc acccaccccc aagaggggcc ttcagctttg gggctcagag gcacgacctc      60
ctggggaggg ttaaaaggca gacgcccccc cgccccccgc gccccgcgc cccgactcct     120 tcgccgcctc cagcctctcg ccagtgggaa gcggggagca gccgcgcggc cggagtccgg     180
aggcgagggg aggtcggccg caacttcccc ggtccacctt aagaggacga tgtagccagc     240
tcgcagcgct gaccttagaa aaacaagttt gcgcaaagtg gagcggggac ccggcctctg     300
ggcagccccg gcggcgcttc cagtgccttc cagccctcgc gggcggcgca gccgcggccc     360
atggagcccg ccggcccggc ccccggccgc ctcgggccgc tgctctgcct gctgctcgcc     420
gcgtcctgcg cctggtcagg agtggcgggt gaggaggagc tgcaggtgat tcagcctgac     480
aagtccgtgt tggttgcagc tggagagaca gccactctgc gctgcactgc gacctctctg     540
atccctgtgg ggcccatcca gtggttcaga ggagctggac caggccggga attaatctac     600
aatcaaaaag aaggccactt cccccgggta acaactgttt cagacctcac aaagagaaac     660
aacatggact tttccatccg catcggtaac atcaccccag cagatgccgg cacctactac     720
tgtgtgaagt tccggaaagg agcccccgat gacgtggagt ttaagtctgg agcaggcact     780
gagctgtctg tgcgcgccaa accctctgcc ccgtggtat cgggccctgc ggcgagggcc     840
acacctcagc acacagtgag cttcacctgc gagtcccacg gcttctcacc cagagacatc     900
accctgaaat ggttcaaaaa tgggaatgag ctctcagact ccagaccaa cgtgaccccc     960 gtaggagaga gcgtgtccta cagcatccac agcacagcca aggtggtgct gacccgcgag    1020
gacgttcact ctcaagtcat ctgcgaggtg gcccacgtca ccttgcaggg ggaccctctt    1080
cgtgggactg ccaacttgtc tgagaccatc cgagttccac ccaccttgga ggttactcaa    1140
cagcccgtga gggcagagaa ccaggtgaat gtcacctgcc aggtgaggaa gttctacccc    1200
cagagactac agctgacctg gttggagaat ggaaacgtgt cccggacaga aacggcctca    1260
accgttacag agaacaagga tggtacctac aactggatga ctggctcct ggtgaatgta    1320 tctgcccaca gggatgatgt gaagctcacc tgccaggtgg agcatgacgg gcagccagcg    1380
gtcagcaaaa gccatgacct gaaggtctca gcccacccga aggagcaggg ctcaaatacc    1440
gccgctgaga cactggatc taatgaacgg aacatctata ttgtggtggg tgtggtgtgc    1500
accttgctgg tggccctact gatggcggcc ctctacctcg tccgaatcag acagaagaaa    1560
gcccagggct ccacttcttc tacaaggttg catgagcccg agaagaatgc cagagaaata    1620
acacaggaca caaatgatat cacatatgca gacctgaacc tgcccaaggg gaagaagcct    1680
gctccccagg ctgcggagcc caacaaccac acggagtatg ccagcattca gaccagcccg    1740
cagcccgcgt cggaggacac cctcacctat gctgacctgg acatggtcca cctcaaccgg    1800 accccccaagc agccggcccc caagcctgag ccgtccttct cagagtacgc cagcgtccag    1860
gtcccgagga agtgaatggg accgtggttt gctctagcac ccatctctac gcgctttctt    1920
gtcccacagg gagccgccgt gatgagcaca gccaacccag ttcccggagg gctggggcgg    1980
```

```
tgcaggctct gggacccagg ggccagggtg gctcttctct ccccacccct ccttggctct    2040
ccagcacttc ctgggcagcc acggccccct cccccacat tgccacatac ctggaggctg     2100
acgttgccaa accagccagg gaaccaacct gggaagtggc cagaactgcc tggggtccaa    2160
gaactcttgt gcctccgtcc atcaccatgt gggttttgaa gaccctcgac tgcctccccg    2220
atgctccgaa gcctgatctt ccagggtggg gaggagaaaa tcccacctcc cctgacctcc    2280
accacctcca ccaccaccac caccaccacc accaccacta ccaccaccac caactggggt   2340
ctagagtggg gaagatttcc cctttagatc aaactgcccc ttccatggaa aagctggaaa    2400
aaaactctgg aacccatatc caggcttggt gaggttgctg ccaacagtcc tggcctcccc    2460
catccctagg ctaaagagcc atgagtcctg gaggaggaga ggacccctcc caaggactg     2520 gagacaaaac cctctgcttc cttgggtccc tccaagactc cctggggccc aactgtgttg    2580
ctccacccgg acccatctct cccttctaga cctgagcttg cccctccagc tagcactaag    2640
caacatctcg ctgtggacgc ctgtaaatta ctgagaaatg tgaaacgtgc aatcttgaaa    2700
ctgaggtgtt agaaaacttg atctgtggtg ttttgttttg ttttttttct taaaacaaca    2760
gcaacgtgat cttggctgtc tgtcatgtgt tgaagtccat ggttgggtct tgtgaagtct    2820
gaggtttaac agtttgttgt cctggaggga ttttcttaca gcgaagactt gagttcctcc    2880
aagtcccaga accccaagaa tgggcaagaa ggatcaggtc agccactccc tggagacaca    2940
gccttctggc tgggactgac ttggccatgt tctcagctga gccacgcggc tggtagtgca    3000
gccttctgtg acccgctgt ggtaagtcca gcctgcccag ggctgctgag ggctgcctct     3060
tgacagtgca gtcttatcga gacccaatgc ctcagtctgc tcatccgtaa agtggggata    3120
gtgaagatga caccctccc caccacctct cataagcact ttaggaacac acagagggta     3180
gggatagtgg ccctggccgt ctatcctacc cctttagtga ccgcccccat cccggctttc    3240
tgagctgatc cttgaagaag aaatcttcca tttctgctct caaaccctac tgggatcaaa    3300
ctggaataaa ttgaagacag ccaggggat ggtgcagctg tgaagctcgg gctgattccc     3360
cctctgtccc agaaggttgg ccagagggtg tgacccagtt accctttaac ccccacccctt   3420 ccagtcgggt gtgagggcct gaccgggccc agggcaagca gatgtcgcaa gcctattta    3480 ttcagtcttc actataactc ttagagttga gacgctaatg ttcatgactc ctggccttgg    3540
gatgcccaag ggatttctgg ctcaggctgt aaaagtagct gagccatcct gcccattcct    3600
ggaggtccta caggtgaaac tgcaggagct cagcatagac ccagctctct gggggatggt    3660
cacctggtga tttcaatgat ggcatccagg aattagctga gccaacagac catgtggaca    3720
gctttggcca gagctcccgt gtggcatctg ggagccacag tgacccagcc acctggctca    3780
ggctagttcc aaattccaaa agattggctt gtaaaccttc gtctccctct cttttaccca    3840
gagacagcac atacgtgtgc acacgcatgc acacacacat tcagtattt aaaagaatgt     3900 tttcttggtg ccattttcat tttatttttat ttttaattc ttggagggg aaataaggga     3960 ataaggccaa ggaagatgta tagctttagc tttagcctgg caacctggag aatccacata    4020
ccttgtgtat tgaaccccag gaaaaggaag aggtcgaacc aaccctgcgg aaggagcatg    4080
gtttcaggag tttattttaa gactgctggg aaggaaacag gccccatttt gtatatagtt    4140
gcaacttaaa cttttttggct tgcaaaatat ttttgtaata aagatttctg ggtaataatg    4200
a                                                                    4201

<210> SEQ ID NO 4
```

<211> LENGTH: 504
<212> TYPE: PRT
<213> ORGANISM: Homo sapiens

<400> SEQUENCE: 4

```
Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Ala Ala Gly
        35                  40                  45

Glu Thr Ala Thr Leu Arg Cys Thr Ala Thr Ser Leu Ile Pro Val Gly
50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr Ile Val Val Gly Val Val Cys Thr Leu Leu Val
    370                 375                 380

Ala Leu Leu Met Ala Ala Leu Tyr Leu Val Arg Ile Arg Gln Lys Lys
```

```
                385                 390                 395                 400
Ala Gln Gly Ser Thr Ser Ser Thr Arg Leu His Glu Pro Lys Asn
                405                 410                 415

Ala Arg Glu Ile Thr Gln Asp Thr Asn Asp Ile Thr Tyr Ala Asp Leu
                420                 425                 430

Asn Leu Pro Lys Gly Lys Lys Pro Ala Pro Gln Ala Ala Glu Pro Asn
                435                 440                 445

Asn His Thr Glu Tyr Ala Ser Ile Gln Thr Ser Pro Gln Pro Ala Ser
                450                 455                 460

Glu Asp Thr Leu Thr Tyr Ala Asp Leu Asp Met Val His Leu Asn Arg
465                 470                 475                 480

Thr Pro Lys Gln Pro Ala Pro Lys Pro Glu Pro Ser Phe Ser Glu Tyr
                485                 490                 495

Ala Ser Val Gln Val Pro Arg Lys
                500
```

<210> SEQ ID NO 5
<211> LENGTH: 508
<212> TYPE: PRT
<213> ORGANISM: Homo sapiens

<400> SEQUENCE: 5

```
Met Glu Pro Ala Gly Pro Ala Pro Gly Arg Leu Gly Pro Leu Leu Leu
1               5                   10                  15

Cys Leu Leu Leu Ser Ala Ser Cys Phe Cys Thr Gly Val Ala Gly Glu
                20                  25                  30

Glu Glu Leu Gln Val Ile Gln Pro Asp Lys Ser Val Leu Val Ala Ala
                35                  40                  45

Gly Glu Thr Ala Thr Leu Arg Cys Thr Ala Thr Ser Leu Ile Pro Val
                50                  55                  60

Gly Pro Ile Gln Trp Phe Arg Gly Ala Gly Pro Gly Arg Glu Leu Ile
65                  70                  75                  80

Tyr Asn Gln Lys Glu Gly His Phe Pro Arg Val Thr Thr Val Ser Asp
                85                  90                  95

Leu Thr Lys Arg Asn Asn Met Asp Phe Ser Ile Arg Ile Gly Asn Ile
                100                 105                 110

Thr Pro Ala Asp Ala Gly Thr Tyr Tyr Cys Val Lys Phe Arg Lys Gly
                115                 120                 125

Ser Pro Asp Asp Val Glu Phe Lys Ser Gly Ala Gly Thr Glu Leu Ser
                130                 135                 140

Val Arg Ala Lys Pro Ser Ala Pro Val Val Ser Gly Pro Ala Ala Arg
145                 150                 155                 160

Ala Thr Pro Gln His Thr Val Ser Phe Thr Cys Glu Ser His Gly Phe
                165                 170                 175

Ser Pro Arg Asp Ile Thr Leu Lys Trp Phe Lys Asn Gly Asn Glu Leu
                180                 185                 190

Ser Asp Phe Gln Thr Asn Val Asp Pro Val Gly Glu Ser Val Ser Tyr
                195                 200                 205

Ser Ile His Ser Thr Ala Lys Val Val Leu Thr Arg Glu Asp Val His
                210                 215                 220

Ser Gln Val Ile Cys Glu Val Ala His Val Thr Leu Gln Gly Asp Pro
225                 230                 235                 240

Leu Arg Gly Thr Ala Asn Leu Ser Glu Thr Ile Arg Val Pro Pro Thr
                245                 250                 255
```

```
Leu Glu Val Thr Gln Gln Pro Val Arg Ala Glu Asn Gln Val Asn Val
                260                 265                 270

Thr Cys Gln Val Arg Lys Phe Tyr Pro Gln Arg Leu Gln Leu Thr Trp
            275                 280                 285

Leu Glu Asn Gly Asn Val Ser Arg Thr Glu Thr Ala Ser Thr Val Thr
        290                 295                 300

Glu Asn Lys Asp Gly Thr Tyr Asn Trp Met Ser Trp Leu Leu Val Asn
305                 310                 315                 320

Val Ser Ala His Arg Asp Asp Val Lys Leu Thr Cys Gln Val Glu His
                325                 330                 335

Asp Gly Gln Pro Ala Val Ser Lys Ser His Asp Leu Lys Val Ser Ala
            340                 345                 350

His Pro Lys Glu Gln Gly Ser Asn Thr Ala Ala Asp Asn Asn Ala Thr
        355                 360                 365

His Asn Trp Asn Val Phe Ile Gly Val Gly Val Ala Cys Ala Leu Leu
    370                 375                 380

Val Val Leu Leu Met Ala Ala Leu Tyr Leu Leu Arg Ile Lys Gln Lys
385                 390                 395                 400

Lys Ala Lys Gly Ser Thr Ser Ser Thr Arg Leu His Glu Pro Glu Lys
                405                 410                 415

Asn Ala Arg Glu Ile Thr Gln Ile Gln Asp Thr Asn Asp Ile Asn Asp
            420                 425                 430

Ile Thr Tyr Ala Asp Leu Asn Leu Pro Lys Glu Lys Lys Pro Ala Pro
        435                 440                 445

Arg Ala Pro Glu Pro Asn Asn His Thr Glu Tyr Ala Ser Ile Glu Thr
    450                 455                 460

Gly Lys Val Pro Arg Pro Glu Asp Thr Leu Thr Tyr Ala Asp Leu Asp
465                 470                 475                 480

Met Val His Leu Ser Arg Ala Gln Pro Ala Pro Lys Pro Glu Pro Ser
                485                 490                 495

Phe Ser Glu Tyr Ala Ser Val Gln Val Gln Arg Lys
            500                 505

<210> SEQ ID NO 6
<211> LENGTH: 200
<212> TYPE: DNA
<213> ORGANISM: Artificial Sequence
<220> FEATURE:
<223> OTHER INFORMATION: Synthetic Oligonucleotide

<400> SEQUENCE: 6
agctctccta ccactagact gctgagaccc gctgctctgc tcaggactcg atttccagta      60
cacaatctcc ctctttgaaa agtaccacac atcctggggt gctcttgcat ttgtgtgaca     120
ctttgctagc caggctcagt cctgggttcc aggtgggac tcaaacacac tggcacgagt     180
ctacattgga tattcttggt                                                 200

<210> SEQ ID NO 7
<211> LENGTH: 199
<212> TYPE: DNA
<213> ORGANISM: Artificial Sequence
<220> FEATURE:
<223> OTHER INFORMATION: Synthetic Oligonucleotide

<400> SEQUENCE: 7
gctccccatt cctcactggc ccagcccctc ttccctactc tttctagccc ctgcctcatc      60
tccctggctg ccattgggag cctgccccac tggaagccag tcgagataac ttcgtataat     120
```

```
gtatgctata cgaagttata tgcatggcct ccgcgccggg ttttggcgcc tcccgcgggc    180
gcccccctcc tcacggcga                                                 199

<210> SEQ ID NO 8
<211> LENGTH: 200
<212> TYPE: DNA
<213> ORGANISM: Artificial Sequence
<220> FEATURE:
<223> OTHER INFORMATION: Synthetic Oligonucleotide

<400> SEQUENCE: 8
cattctcagt attgttttgc caagttctaa ttccatcaga cctcgacctg cagcccctag     60
ataacttcgt ataatgtatg ctatacgaag ttatgctagc tgtctcatag aggctggcga    120
tctggctcag ggacagccag tactgcaaag agtatccttg ttcataccct ctcctagtgg    180
ccatctccct gggacagtca                                                200
```